US012805714B2

(12) United States Patent
Jones et al.

(10) Patent No.: US 12,805,714 B2

(45) Date of Patent: Nov. 24, 2026

(54) ORAL IMAGING SYSTEM AND METHOD OF ANALYZING A TOOTH

(71) Applicant: GREENMARK BIOMEDICAL INC., East Lansing, MI (US)

(72) Inventors: Kai Alexander Jones, Hamilton (CA); Nathan A. Jones, Ann Arbor, MI (US); Steven Bloembergen, Okemos, MI (US); Scott Raymond Pundsack, Georgetown (CA); Yu Cheng Lin, Toronto (CA); Helmut Neher, Jr., Welland (CA)

(73) Assignee: GREENMARK BIOMEDICAL INC., East Lansing, MI (US)

( * ) Notice: Subject to any disclaimer, the term of this patent is extended or adjusted under 35 U.S.C. 154(b) by 265 days.

(21) Appl. No.: 18/548,301

(22) PCT Filed: Mar. 4, 2022

(86) PCT No.: PCT/US2022/018953

§ 371 (c)(1),
(2) Date: Aug. 29, 2023

(87) PCT Pub. No.: WO2022/187654

PCT Pub. Date: Sep. 9, 2022

(65) Prior Publication Data

US 2024/0138665 A1 May 2, 2024

Related U.S. Application Data

(60) Provisional application No. 63/157,151, filed on Mar. 5, 2021, provisional application No. 63/157,378, filed on Mar. 5, 2021.

(51) Int. Cl.

*A61B 1/24* (2006.01)
*A61B 1/00* (2006.01)

(Continued)

(52) U.S. Cl.

CPC .......... *A61B 1/24* (2013.01); *A61B 1/000096* (2022.02); *A61B 1/00186* (2013.01);

(Continued)

(58) Field of Classification Search

None

See application file for complete search history.

(56) References Cited

U.S. PATENT DOCUMENTS 4,479,499 A 10/1984 Alfano
6,084,005 A 7/2000 Fukunishi et al.

(Continued)

FOREIGN PATENT DOCUMENTS

EP 2061372 A1 5/2009
EP 2895106 A1 7/2015

(Continued)

OTHER PUBLICATIONS

European Patent Application No. 19857357.8, Partial Supplementary European Search Report dated May 16, 2022.

(Continued)

*Primary Examiner* — Lennin R Rodriguezgonzalez

(57) ABSTRACT

An imaging system, optionally an intra-oral camera, includes a blue light source and a barrier filter over a camera sensor. Optionally, the imaging system can also take white light images. Optionally, the system includes positively charged nanoparticles with fluorescein. The fluorescent nanoparticles can be identified on an image of a tooth by machine vision or machine learning algorithms on a pixel level basis. Either white light or fluorescent images can be used, with machine learning or artificial intelligence algorithms, to score the lesions. However, the white light image is not useful for determining whether lesions, particularly ICDAS 0-2 lesions, are active or inactive. A fluorescent image, with the fluorescent nanoparticles, can be used to (Continued)

detect and score active lesions. Optionally using a white light image and a fluorescent image together allows for all lesions, active and inactive, to be located and scored, and for their activity to be determined.

21 Claims, 7 Drawing Sheets

(51) Int. Cl.

| | |
|---|---|
| ***A61B 1/06*** | (2006.01) |
| ***A61B 5/00*** | (2006.01) |
| ***G16H 30/20*** | (2018.01) |
| ***G16H 30/40*** | (2018.01) |

(52) U.S. Cl.

CPC .......... *A61B 1/0661* (2013.01); *A61B 5/4842* (2013.01); *G16H 30/20* (2018.01); *G16H 30/40* (2018.01)

(56) References Cited

U.S. PATENT DOCUMENTS

| | | | | |
|---|---|---|---|---|
| 6,276,934 | B1 | 8/2001 | Rakocz | |
| 7,365,844 | B2 | 4/2008 | Richards-Kortum et al. | |
| 8,571,397 | B2 | 10/2013 | Liu et al. | |
| 8,982,200 | B2 | 3/2015 | Kitaoka et al. | |
| 9,547,903 | B2 | 1/2017 | Wu et al. | |
| 10,215,977 | B1 | 2/2019 | Feinbloom et al. | |
| 10,987,434 | B2 | 4/2021 | Lahann et al. | |
| 11,150,537 | B2 | 10/2021 | Pikkula et al. | |
| 2004/0202356 | A1 | 10/2004 | Stookey et al. | |
| 2004/0240716 | A1 | 12/2004 | de Josselin de Jong et al. | |
| 2005/0003323 | A1 | 1/2005 | Katsuda et al. | |
| 2008/0038686 | A1 | 2/2008 | Nagai | |
| 2008/0063998 | A1 | 3/2008 | Liang et al. | |
| 2008/0094631 | A1 | 4/2008 | Jung et al. | |
| 2010/0145669 | A1 | 6/2010 | Norden et al. | |
| 2011/0157457 | A1 | 6/2011 | Mo et al. | |
| 2011/0275900 | A1 | 11/2011 | Gilhuly et al. | |
| 2013/0184591 | A1 | 7/2013 | Tesar | |
| 2013/0189641 | A1 | 7/2013 | Perfect et al. | |
| 2013/0323674 | A1 | 12/2013 | Hakomori et al. | |
| 2014/0017625 | A1 | 1/2014 | Liu et al. | |
| 2014/0120499 | A1 | 5/2014 | Nakatsuka et al. | |
| 2015/0107034 | A1 | 4/2015 | Shani et al. | |
| 2015/0250572 | A1 | 9/2015 | Gramann et al. | |
| 2015/0374634 | A1 | 12/2015 | Koo et al. | |
| 2016/0330365 | A1 | 11/2016 | Maruyama et al. | |
| 2017/0112949 | A1 | 4/2017 | Lahann et al. | |
| 2017/0168812 | A1 | 6/2017 | Golay et al. | |
| 2018/0206957 | A1 | 7/2018 | Ruth et al. | |
| 2018/0242848 | A1 | 8/2018 | DaCosta et al. | |
| 2018/0249913 | A1 | 9/2018 | Seibel et al. | |
| 2019/0313963 | A1* | 10/2019 | Hillen .................. | G06V 10/764 |
| 2019/0365236 | A1 | 12/2019 | Van Der Poel | |
| 2020/0008914 | A1 | 1/2020 | Schmid et al. | |
| 2020/0030070 | A1 | 1/2020 | Gerlach et al. | |
| 2020/0175681 | A1* | 6/2020 | Ezhov ..................... | G06T 11/20 |
| 2021/0302314 | A1 | 9/2021 | Kawada et al. | |

FOREIGN PATENT DOCUMENTS

| | | | | | |
|---|---|---|---|---|---|
| WO | 2017070578 | A1 | | 4/2017 | |
| WO | 2017205294 | A1 | | 11/2017 | |
| WO | 2018101977 | A1 | | 6/2018 | |
| WO | WO-2020051352 | A1 | * | 3/2020 | ............. A61C 19/04 |

OTHER PUBLICATIONS

International Application No. PCT/US2022/018953, International Search Report and Written Opinion dated May 3, 2022.

Carestream Health Inc., Intraoral Cameras from Carestream Dental Brochure, 8 pages, 2012.

Carestream Health Inc., Carestream Dental CS 1600 Brochure, 8 pages, 2011.

International Application No. PCT/US2019/049778, International Preliminary Report on Patentability dated Mar. 18, 2021.

International Application No. PCT/US2019/049778, International Search Report and Written Opinion dated Dec. 23, 2019.

European Patent Application No. 19857357.8, Office Action dated Dec. 1, 2023.

European Patent Application No. 22764155.2, Extended European Search Report dated Dec. 6, 2024.

International Application No. PCT/US2022/018953, International Preliminary Report on Patentability dated Aug. 29, 2023.

University of Rochester, "Nanoparticles release drugs to reduce tooth decay", PhysOrg, Apr. 1, 2015 (obtained from: https://phys.org/news/2015-04-nanoparticles-drugs-tooth.html#google_vignette), 3 pages.

Horev et al., "pH-Activated Nanoparticles for Controlled Topical Delivery of Farnesol to Disrupt Oral Biofilm Virulence", ACS Nano, 2015, 9(3), 2390-2404.

Fusayama, T., "Two layers of carious dentin; diagnosis and treatment", Oper. Dent., 1979, 4, 63-70.

Kuboki et al., "Mechanism of differential staining in carious dentin", J. Dent. Res., 1983; 62, 713-4.

Jones, N. et al., "Carious Lesions: Nanoparticle-Based Targeting and Detection of Microcavities", Advanced Healthcare Materials, vol. 6 No. 1, Jan. 11, 2017.

European Patent Application No. 19857357.8, European Search Report dated Sep. 9, 2022.

* cited by examiner

ORAL IMAGING SYSTEM AND METHOD OF ANALYZING A TOOTH

RELATED APPLICATIONS

This application is a National Stage Entry of International Application No. PCT/US2022/018953, filed Mar. 4, 2022, which claims the benefit of U.S. provisional patent application Nos. 63/157,378 and 63/157,151, both filed on Mar. 5, 2021. U.S. provisional patent application Nos. 63/157,378 and 63/157,151 are incorporated herein by reference.

FIELD

This specification relates to dental imaging systems and methods and to systems and methods for caries detection.

BACKGROUND

International Publication Number WO 2017/070578 A1, Detection and Treatment of Caries and Microcavities with Nanoparticles, published on Apr. 27, 2017, describes nanoparticles for detecting active carious lesions in teeth. In some examples the nanoparticles include starch that has been cationized and bonded to a fluorophore, for example fluorescein isomer 1 modified to have an amine functionality. The nanoparticles are positively charged and fluorescent. The nanoparticles can be applied to the oral cavity of a person and selectively attach to active caries lesions. The nanoparticles are excited by a dental curing lamp and viewed through UV-filtering glasses. Digital images were also taken with a digital camera. In some cases, the green channel was extracted for producing an image. Other images were made in a fluorescence scanner with a green 542 nm bandpass filter and blue light illumination.

INTRODUCTION

This specification describes a dental imaging system, for example an intra-oral camera, and methods of using it, optionally in combination with a fluorescent imaging aid applied to a tooth.

In some examples, an imaging system includes a first blue light source and one or more of a red light source, a white light source and a second blue light source. The red light source may also produce other colors of light. For example, the red light source may be a monochromatic red light source, a purple lights source (i.e. a mixture of blue and red light) or a low to medium color temperature white light source. The white source optionally has a color temperature above 3000 K. The second blue light source has a different peak wavelength than the first blue light sources. Images may be produced with any permutation or combination of one or more of these light sources. The system also includes a sensor and a barrier filter. In some examples, the system may produce images with or without light passing through the barrier filter, for example by way of moving the barrier filter.

This specification also describes a method of producing an image of plaque, calculus or active carious lesions in the mouth of a person or other animal, and a method of manipulating or using an image of a tooth. In some examples, a fluorescent area of the image is located using one or more of: hue, intensity, value, blue channel intensity, green channel intensity, a ratio of green and blue channel intensities, a decision tree and/or UNET architecture neural network.

Fluorescent, cationic submicron starch (FOSS) particles can label the subsurface of carious lesions and assist dental professionals in the diagnostic process. This specification describes using machine vision, machine learning (ML) and/or artificial intelligence (AI) to identify a fluorescent area on an image and/or detect and score carious lesions using the ICDAS-II or other system in combination with fluorescent imaging following application of FOSS particles on teeth. In some examples, a range of caries severities may be determined.

DETAILED DESCRIPTION

International Publication Number WO 2020/051352 A1, Dental Imaging and/or Curing System, published on Mar. 12, 2020, is incorporated herein by reference.

Figure 1:
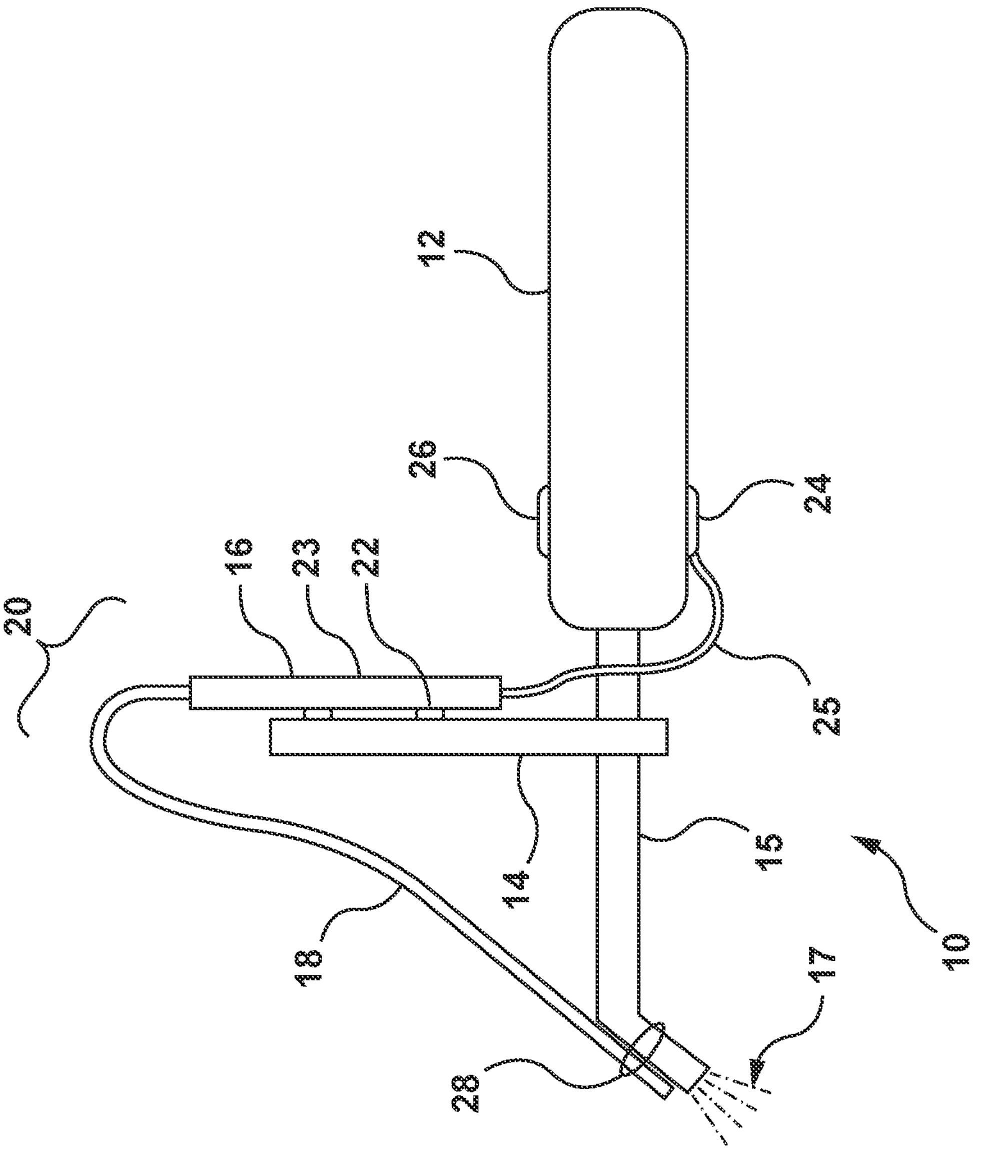
FIG. 1 is a schematic drawing of a dental imaging and/or curing system.

FIG. 1 shows a dental imaging and/or curing system 10. The system 10 has a dental curing light 12, or optionally another source of light or other radiation or electromagnetic waves or waveform energy. The curing light 12 has a plastic plate 14, used to block the light, and a wand 15 where the light 17 is emitted from. An endoscope camera 20 is attached to the curing light 12. Optionally, some or all of the parts of the endoscope camera can be integrated into the curing light. In the example shown, the endoscope camera 20 is made by attaching an endoscope probe 18 to a smartphone 16. One example of an endoscope probe is the USB Phone Endoscope Model DE-1006 from H-Zone Technology Co., Ltd. The smartphone 16, or the body of an endoscope camera preferably having a screen, can be attached to the plate 14 with, for example, two-side tape or hook and loop fastening strips. The endoscope camera 20 can be operated from one or more buttons or touch screens on the smartphone 16 or endoscope camera body. Optionally, a remote button 24 can be attached to the handle of the curing light 12. In the example shown, button 26 is activated, for example by thumb, to turn on light 17 and button 24 is used to take a still picture or start and stop taking a video. In the example shown, button 24 and cable are taken from a disassembled selfie stick. Optionally, a screen of the endoscope camera 20 can be integrated with plastic plate 14. Optionally, endoscope camera 20 could be an intra-oral camera as currently used in dental offices.

The endoscope probe 18 is attached to the wand 15, for example with one or more cable ties 28. The endoscope camera 20 is thereby generally aligned with the end of wand 15 such that the endoscope camera 20 can collect images of an area illuminated by light 17. Optionally, the endoscope probe 18 can be integrated with the wand 15. Optionally, the end of the endoscope camera probe 18 that is placed in the mouth can have an emission filter place over it, as described for the examples below.

In one operating method, the endoscope camera 20 is configured to show a real time image. This image may be recorded as a video while being shown on the screen 23 of the endoscope camera 20, which faces someone holding the curing light 12, or the image may just appear on the screen 23 without being recorded.

The image on screen 23 can be used to help the user point the light 17 at a tooth of interest. When a tooth of interest is in the center of light 17, the tooth of interest will appear brighter than other teeth and be in the center of screen 23. This helps the user aim the light 17. Further, the endoscope camera 20 may include a computer that analyzes images generally as they are received. The computer may be programmed, for example with an app downloaded to smartphone 16, to distinguish between resin and tooth or to allow the user to mark an area having resin. The program determines when the resin is cured. For example, the resin can monitor changing contrast between the resin and tooth while the resin cures and determine when the contrast stops changing.

The light 17 can also be used to illuminate fluorescent nanoparticles, for example as described in the article mentioned above, in lesions in the tooth. The nanoparticles, if any, appear in the image on screen 23 allowing a user to determine if a tooth has an active lesion or not, and to see the size and shape of the lesion. Button 24 can be activated to take a picture or video of the tooth with nanoparticles. Optionally, the image or video can be saved in the endoscope camera 20. Optionally, the image or video can be transferred, at the time of creation or later, to another device such as a general purpose dental office computer or remote server, for example by one or more of USB cable, local wireless such as Wi-Fi or Bluetooth, long distance wireless such as cellular, or by the Internet.

In one example, an app operating in the endoscope camera conveys images, for example all images or only certain images selected by a user, by Wi-Fi or Bluetooth, etc., to an internet router. The internet router conveys the images to a remote, i.e. cloud based, server. The images are stored in the server with one or more related items of information such as date, time, patient identifier, tooth identifier, dental office identifier. The patient is given a code allowing them to retrieve copies of the images, for example by way of an app on their phone, or to transmit a copy to their insurer or authorize their insurer to retrieve them. Alternatively, a dental office person may transmit the images to an insurer or authorize the insurer to retrieve them. An app on the patient's smartphone may also be used to receive reminders, for example of remineralization treatments prescribed by a dentist to treat the lesions shown in the images. A dental office person may also log into the remote server to view the images.

The remote server also operates image analysis software. The image analysis software may operate automatically or with a human operator. The image analysis software analysis photographs or video of teeth to, for example, enhance the image, quantify the area of a part of the tooth with nanoparticles, or outline and/or record the size and/or shape of an area with nanoparticles. The raw, enhanced or modified images can be stored for comparison with similar raw, enhanced or modified images taken at other times to, for example, determine if a carious lesion (as indicated by the nanoparticles) is growing or shrinking in time.

In one example, an operator working at the remote server or in the dental office, uses software operating on any computer with access to images take of the same tooth at two different times. The operator selects two or more distinguishing points on the tooth and marks them in both images. The software computes a difference in size and orientation of the tooth in the images. The software scans the image of the tooth to distinguish between the nanoparticle containing area and the rest of the tooth. The software calculates the relative area of the nanoparticle containing area adjusting for differences in size and orientation of the whole tooth in the photo. In one example, a remote operator sends the dental office a report of change of size in the lesion. In other examples, some or all of these steps are automated.

In another example, data conveyed to the remote server may be anonymized and correlated to various factors such as whether water local to the patient is fluoridized, tooth brushing protocols or remineralization treatments. This data may be analyzed to provide reports or recommendations regarding dental treatment.

Reference to a remote server herein can include multiple computers.

Figure 2:
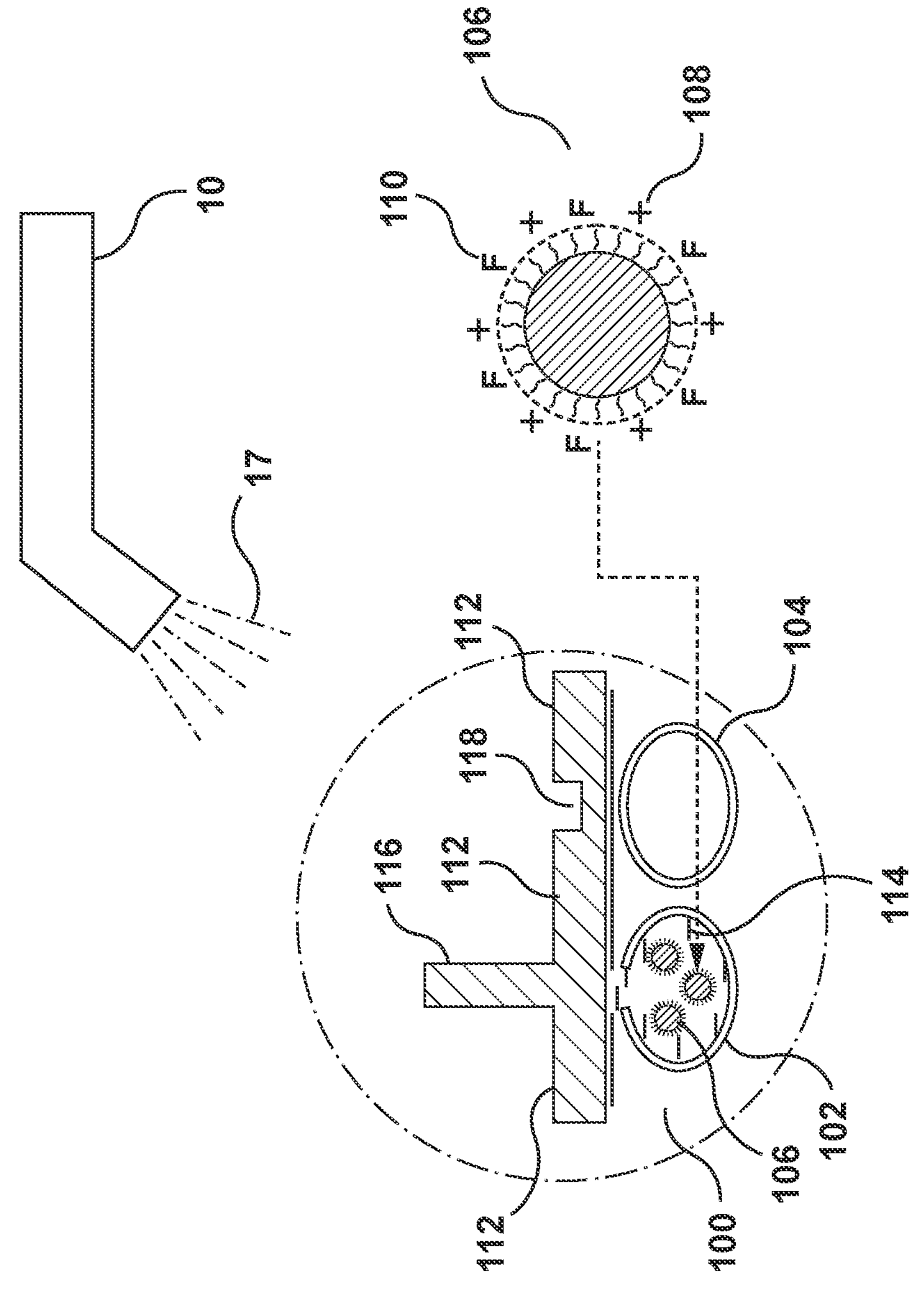
FIG. 2 is a pictorial representation of use of the system of FIG. 1 to detect active carious lesions, and to distinguish them from inactive lesions, which may be re-mineralized lesions.

FIG. 2 shows one possible use of the system 10 or any of other systems described herein. The system shines light 17 (or other waves, radiation, etc.) on a tooth 100. In FIG. 2, numeral 100 shows the enamel of a tooth having an active lesion 102 and an inactive lesion 104. Lesions 102, 104 might alternatively be called caries or cavities or microcavities. Active lesion 102 might be less than 0.5 mm deep or less than 0.2 mm deep, in which case it is at least very difficult to detect by dental explorer and/or X-ray. The inactive lesion 104 may be an active lesion 102 that has become re-mineralized due to basic dental care (i.e. drinking water with fluoride, brushing teeth with fluoride containing toothpaste, routine dental fluoride treatment) or a targeted re-mineralizing treatment. FIG. 2 is schematic and inactive lesion 104 could exist at the same time and on the same tooth as active lesion 102, at the same time as active lesion 102 but in a different tooth, or at a different time as active lesion 102. In one example, inactive lesion 104 is a future state of active lesion 102. In this case, inactive lesion 104 is in the same area of the same tooth 100 as active lesion 102, but inactive lesion 104 exists at a later time.

A fluorescent imaging aid such as nanoparticle 106, optionally a polymer not formed into a nanoparticle, optionally a starch or other polymer or nanoparticle that is biodegradable and/or biocompatible and/or biobased, is contacted with tooth 100 prior to or while shining light 17 on the tooth. For example, nanoparticle 106 can be suspended in a mouth rinse swished around a mouth containing the tooth or applied to the tooth directly, ie. with an applicator, as a suspension, gel or paste. Nanoparticle 106 is preferably functionalized with cationic moieties 108. Nanoparticle 106 is preferably functionalized with fluorescent moieties 110. The active lesion 102 preferentially attracts and/or retains nanoparticles 106. This may be caused or enhanced by one or more an electrostatic effect due to negative charges 114 associated with active lesion 102 and physical entrapment of nanoparticles 106 inside the porous structure of active lesion 102. The nanoparticle 106 may be positively charged, for example it may have a positive zeta potential at either or both of the pH of saliva in the oral cavity (i.e. about 7, or in the range of 6.7 to 7.3), or at a lower pH (i.e. in the range of 5 to 6) typically found in or around active carious lesions.

Shining light 17 on tooth 100 causes the tooth to emit fluorescence, which is recorded in an image, i.e. a photograph, recorded and/or displayed by system 10. Normal enamel of the tooth emits a background fluorescence 112 of a baseline level. The active lesion 102, because it has nanoparticles 106, emits enhanced fluorescence 116, above the baseline level. Inactive lesion 104 has a re-mineralized surface that emits depressed fluorescence 118 below the baseline level.

Analyzing the image produced by system 10 allows an active lesion 102 to be detected by way of its enhanced fluorescence 116. The image can be one or more of stored, analyzed, and transmitted to a computer such as a general purpose computer in a dental office, an off-site server, a dental insurance company accessible computer, or a patient accessible computer. The patient accessible computer may optionally be a smart phone, also programmed with an app to remind the patient of, for example, a schedule of re-mineralizing treatments. In a case where re-mineralizing treatments are applied to tooth 100, active lesion 102 may become an inactive lesion 104.

Comparing images made at different times, particularly before and after one or more re-mineralizing treatments, allows the re-remineralizing progress to be monitored. Increasing fluorescence at a specified area of tooth 100 indicates that the lesion is worsening, and might need a filling. Stable or decreasing fluorescence indicates that remineralization treatment is working or at least that the tooth 100 is stable. A conversion from enhanced fluorescence 116 to depressed fluorescence 118 suggests completed remineralization. Comparison of images can be aided on or more of a) recording images, so that images of tooth 100 taken at different times can be view simultaneously, b) rotating and or scaling an image of tooth 100 to more closely approximate or match the size or orientation of another image of tooth 100, c) adjusting the intensity of an image of tooth 100 to more closely approximate or match the size or orientation of another image of tooth 100, for example by making the background fluorescence 112 in the two images closer to each other, d) quantifying the size (i.e. area) of an area of enhanced fluorescence 116, e) quantifying the intensity of an area of enhanced fluorescence 116, for example relative to background fluorescence 112.

The imaging aid such as nanoparticle 106 preferably contains fluorescein or a fluorescein based compound. Fluorescein has a maximum adsorption of 494 nm or less and maximum emission at 512 nm or more. However the light 17 can optionally comprise any light in about the blue (about 475 nm or 360-480 nm) range, optionally light in the range of 400 nm to 500 nm or in the range of 450 nm to 500 nm or in the range of about 475 nm to about 500 nm. The camera 20 is optionally selective for green (i.e. about 510 nm, or in a range of 500 to 525 nm) light, for example by including a green passing emission filter, or alternatively or additionally the image from camera 20 can be filtered to selectively show green light, i.e. the green channel can be selected in image analysis software.

For example, an image from a general-purpose camera can be manipulated to select a green pixel image. The system can optionally employ a laser light for higher intensity, for example a blue laser, for example a 445 nm or 488 nm or other wavelength diode (diode-pumped solid state or DPSS) laser.

Figure 3:
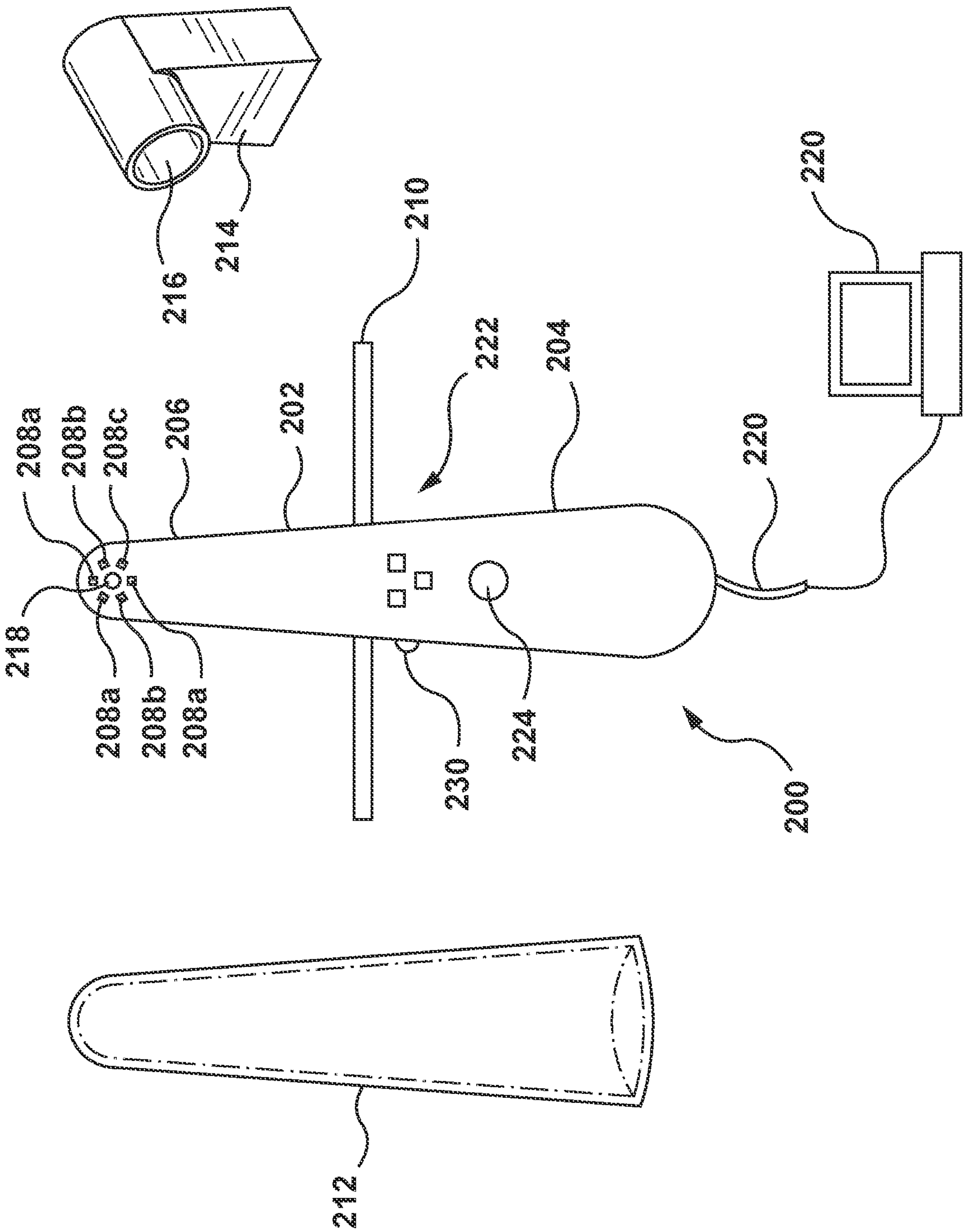
FIG. 3 shows an alternative system.

FIG. 3 shows an alternative intra-oral device 200 for use in the system 10. The device 200 provides a light and a camera like the device shown in FIG. 1 but in a different form. Any elements or steps described herein (for example with FIG. 1 or 2 or elsewhere above or it the claims) can be used with device 200 and any elements or steps described in association with FIG. 3 can be used with the system 10 or anything else disclosed herein.

Device 200 has a body 202 that can be held in a person's hand, typically at first end 204. Optionally a grip can be added to first end 204 or first end 204 can be formed so as to be easily held. Second end 206 of body 202 is narrow, optionally less than 25 mm or less than 20 mm or less than 15 mm wide, and can be inserted into a patient's mouth.

Second end 206 has one or more lights 208. The lights can include one or more blue lights, optionally emitting in a wavelength range of 400-500 nm or 450-500 nm. Optionally, one or more lights, for example lights **208*a*, can be blue lights while one or more other lights, for example lights 208*b*, can be white or other color lights. Lights 208*a*, 208*b*, can be for example, LEDs. Optionally, one or more lights for example light 208*c*, can be a blue laser, for example a diode or DPSS laser, optionally emitting in a wavelength range of 400-500 nm or 450-500 nm. One or more of lights 208 can optionally be located anywhere in body 200 but emit at second end 206 through a mirror, tube, fiber optic cable or other light conveying device. Optionally, one or more lights 208** can emit red light. Red light can be provided from a monochromatic red LED, a purple LED (i.e. an LED that produces red and blue light) or a white LED, for example a warm or low-medium (3000 K or less) white LED. Associated software can be used to interpret images taken under red light to detect the presence or deep enamel or dentin caries. Alternatively, red light added to a primarily blue light image can be used to increase the overall brightness of the image and/or to increase the visibility of tissue around the tooth. Increased brightness may help to prevent a standard auto-exposure function of a camera from over exposing, i.e. saturating, the fluorescent area of an image. Red light added to a primarily blue light image may also increase a hue differential between intact enamel and a lesion, thereby helping to isolate a fluorescent area in an image by machine vision methods to be described further below.

Optionally, device 200 has an ambient light blocker or screen 210, optionally and integrated ambient light blocker and screen. For hygiene, a sleeve 212, for example a disposable clear plastic sleeve, can be placed over some or all of device 200 before it is placed in a patient's mouth. Optionally, a second ambient light blocker 214 can be placed over the second end 206 to direct light through hole 216 towards a tooth and/or prevent ambient light from reaching a tooth.

Device 200 has one or more cameras 218. Camera 218 captures images of a tooth or teeth illuminated by one or more lights 208. Images from camera 218 can be transmitted by cord 220, or optionally Bluetooth, Wi-Fi or other wireless signal, to computer 220. Images can also be displayed on screen 210 or processed by a computer or other controller, circuit, hardware, software or firmware located in device 200. Various buttons 222 or other devices such as switches or touch capacitive sensors are available to allow a person to operate lights 208 and camera 218. Optionally, camera 218 can be located anywhere in body 200 but receive emitted light through a mirror, tube, fiber optic cable or other light conveying device. Camera 218 may also have a magnifying and/or focusing lens or lenses.

Optionally device 200 has a touch control 224, which comprises a raised, indented or otherwise touch distinct surface with multiple touch sensitive sensors, such as pressure sensitive or capacitive sensors, arranged on the surface. The sensors in the touch control 224 allow a program running in computer 220 or device 200 to determine where a person's finger is on touch control 224 and optionally to sense movements such as swipes across the touch control 224 or rotating a finger around the touch control 224. These touches or motions can be used, in combination with servos, muscle wire, actuators, transducers or other devices, to control one or more lights 208 or cameras 218, optionally to direct them (i.e. angle a light 208 or camera 218 toward a tooth) or to focus or zoom a camera 218.

Device 200 can optionally have an indicator 230 that indicates when a camera 218 is viewing an area of high fluorescence relative to background. Indicator 230 may be, for example, a visible light or a synaptic indicator that creates a pulse or other indication that can be seen or felt by a finger. The user is thereby notified that a tooth of interest is below a camera 218. The user can then take a still picture, record a video, or look up to a screen to determine if more images should be viewed or recorded. Optionally, the device 200 may automatically take a picture or video recording whenever an area of high fluorescence is detected.

Figure 4:
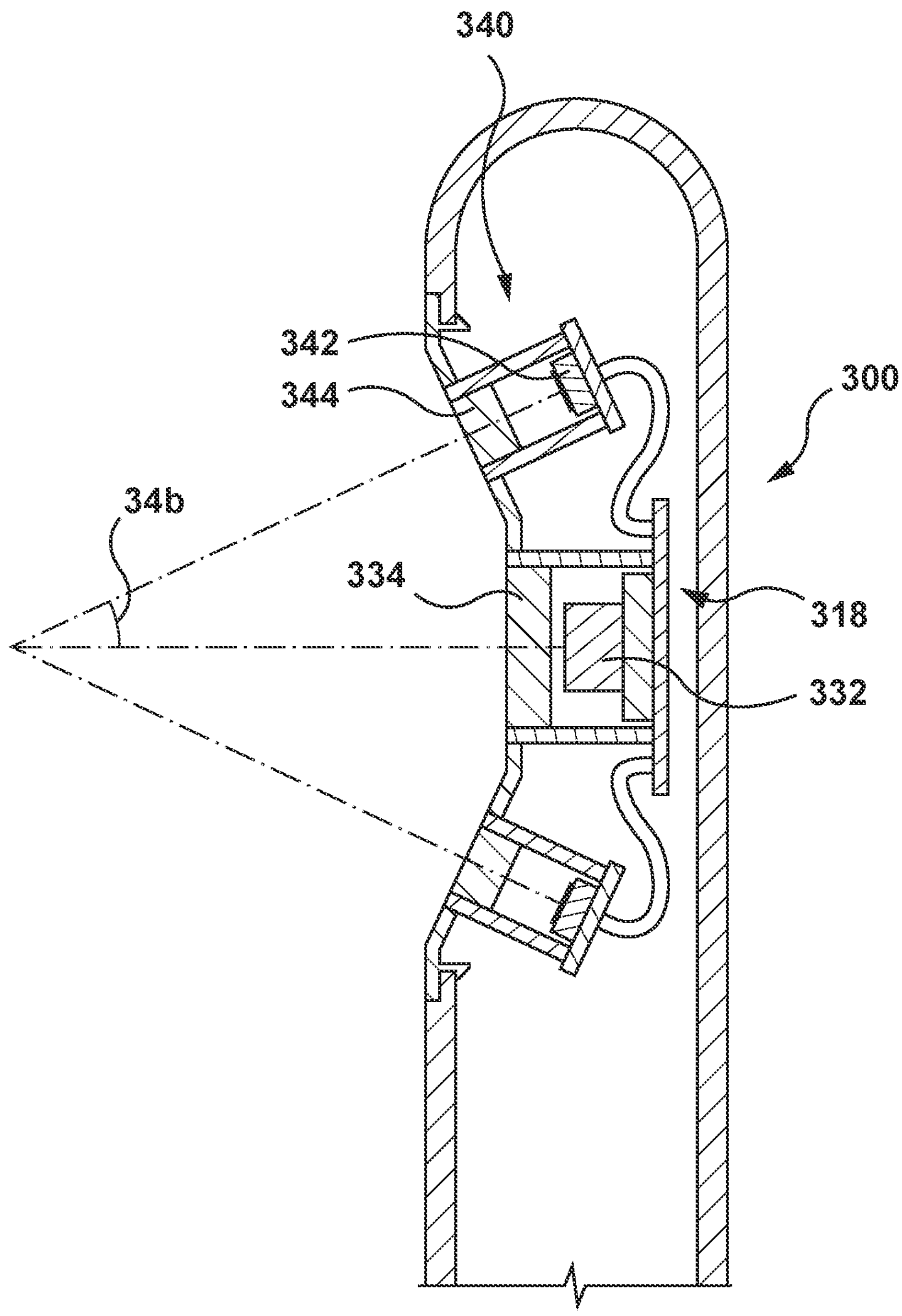
FIG. 4 shown another alternative system.

FIG. 4 shows part of an alternative intra-oral device 300 for use in the system 10. The device 300 provides a light and a camera like the device shown in FIG. 1 but in a different form. Any elements or steps described herein (for example with FIG. 1 or 2 or 3 or elsewhere above or it the claims) can be used with device 300 and any elements or steps described in association with FIG. 4 can be used with the system 10 or anything else disclosed herein. In particular, the part of device 300 shown in FIG. 4 can be used as a replacement for second end 206 in the device 200.

Device 300 has a camera 318 including an image sensor 332 and an emission filter 334 (alternatively called a barrier filter). The image sensor 332 may be a commercially available sensor sold, for example, as a digital camera sensor. Image sensor 332 may include, for example a single channel sensor, such as a charge-coupled device (CCD), or a multiple channel (i.e. red, blue green (RGB)) sensor. The multiple channel sensor may include, for example, an active pixel sensor in complementary metal-oxide-semiconductor (CMOS) or N-type metal-oxide-semiconductor (NMOS) chip. The image sensor 332 can also have one or more magnification and/or focusing lenses, for example one or more lenses as are frequently provided on small digital cameras, for example as in a conventional intra-oral camera with autofocus capability. For example, the image sensor 332 can have an auto-focusing lens. The camera 318 can also have an anti-glare or polarizing lens or coating. While a single channel image sensor 332 is sufficient to produce a useful image, in particular to allow an area of fluorescence to be detected and analyzed, the multiple channel image can also allow for split channel image enhancement techniques either for analysis of the area of fluorescence or to produce a visual display that is more readily understandable to the human eye.

Device 300 also has one or more light sources 340. The light source 340 includes a lamp 342. The light source 340 optionally includes an excitation filter 344. The lamp 342 can be, for example, a light-emitting diode (LED) lamp. The light source can produce white or blue light. In some examples, a blue LED is used. In one alternative, a blue LED with peak emission at 475 nm or less is used, optionally with an excitation filter 344, in order to produce very little light at a wavelength that will be detected by the camera 318, which is selective for light above for example 510 nm, or above 520 nm. In another alternative, a blue LED with peak emission in the range of 480-500 nm (which are available for example in salt water aquarium lighting devices) is used. While a higher frequency blue LED is likely to produce more light that overlaps with the selective range of the camera (compared to a similar blue LED with lower peak emission frequency), a higher frequency blue LED can optionally be used in combination with a short pass or bandpass filter that transmits only 50% or less or 90% or less of peak transmittance of light above a selected wavelength, for example 490 nm or 500 nm or 510 nm. Filters specified by their manufacturers according to 50% of peak transmission tend to be absorption filters with low slope cut-on or cut-off curves while filters specified by their manufacturers according to 90% (or higher) of peak transmittance tend to be dichromic or other steep slope filters that will cut-off sharply outside of their nominal bandwidth. Accordingly, either standard of specification may be suitable. Suitable high frequency blue LEDs may be sold as cyan, turquoise, blue-green or bluish-green lights. In addition to being closer the peak excitation frequency of fluorescein, such high frequency LEDs may produce less excitation of tooth enamel, which has a broad excitation curve peak including lower frequencies. For similar reasons, a bandpass excitation filter may be advantageous over a lowpass excitation filter in reducing tooth enamel fluorescence and useful even with a blue LED of any color.

Optionally, excitation filter 334 may be a bandpass filter with the upper end of its band in the range of 490-510 nm, or 490-500 nm, defined by 50% or 90% of peak transmission. Excitation filter 334 may have a bandwidth (i.e. FWHM) in the range of up to 60 nm, for example 20-60 nm or 30-50 nm, defined by 50% or 90% of peak transmission. Optional excitation filters are Wratten 47 and Wratten 47A sold by Kodak, Tiffen or others or a dichromic filter having a center (CWL) of 450-480 nm, optionally 465-475 nm, and a bandwidth (FWHM) of 20-60 nm, optionally 30-50 nm, wherein the bandwidth is defined by either transmission of 50% of peak or 90% of peak.

The light source 340 can optionally be pointed towards a point in front of the camera 318. For example, a pre-potted cylindrical, optionally flat-topped, or surface mount LED can be placed into a cylindrical recess. In the example shown in FIG. 4, a surface mounted blue LED is located at the bottom of a hole, in particular a tube formed in an insert that includes the camera 318. A cylindrical excitation filter 344 is optionally placed over the LED 342 in the tube. Precise direction of the emitted light is not required. However, to help reduce the amount of reflected light that reaches the sensor, the hole can have an aspect ratio of at least 1 (i.e. a length of 5 mm or more when the diameter is 5 mm), or 1.5 or more, or 2 or more. The LED 342 can be aimed at an angle 346 that is at least 20 degrees apart from an aiming line of the sensor 332. Alternatively, a commercially available lensed LED 342 (i.e. an LED pre-potted in a resin block) with a viewing angle of 45 degrees or less may be used. There may be one light source or, as shown for example in FIG. 4, 2 light sources can be used. Optionally, there may be 3 or more light sources.

The camera 318 optionally includes a longpass or bandpass barrier filter 334. In some previous work as described in the background section, photographs were taken through orange filters of the type used in goggles to protect the eyes of dental professionals from blue curing lamps. Useful images of extracted teeth were obtained, particularly in combination with green pixel only image modification, from a conventional digital camera. These orange filters are longpass filters, but with somewhat high cut-offs as is appropriate for eye protection. For example, UVEX™ SCT-Orange™ goggles have a cut-on frequency of about 550 nm. Transmission through these goggles at the fluorescein emission peak of 521 nm is very low (i.e. less than 5% of peak) and transmission even at 540 nm is still less than 25% of peak.

Images can be improved by using a longpass filter with a lower cut-on frequency, for example a cut-on frequency of in the range of 510-530 nm. For example, a Wratten 12 yellow filter or Wratten 15 orange filter, produced by or under license from Kodak or by others, may be used.

Further improved imaging can be achieved by using a bandpass filter with 50% transmission or more or 90% transmission or more in a pass band starting in the range of 510-530 nm, for example at 515 nm or more or 520 nm or more. The center frequency (CWL) may be in the range of 530-550 nm. The use of a bandpass filter is preferred over a longpass filter because tooth enamel has a broad emission spectra with material emission above 560 nm. The barrier filter 334 maybe a high quality filter, for example a dichromic filter, with sharp cut-offs.

In the examples above, the teeth are preferably cleaned before applying the nanoparticles to the teeth to remove excess plaque and/or calculus. This removes barriers to the nanoparticles entering active lesions and reduces interfering fluorescence from the plaque or calculus itself. Similarly, the nanoparticles may enter a crack in a tooth and allow for taking an image of the crack. Alternatively, the plaque and/or calculus can be left in place and the device 10, 200, 300 can be used to image the plaque or calculus. The nanoparticles may be applied to adhere to the plaque and/or calculus. Alternatively, an aqueous fluorescein solution may be used instead of the nanoparticles to increase the fluorescence of plaque and/or calculus. The fluorescein in such a solution does not need to be positively charged.

In the discussion above, the word "nanoparticles" refers to particles having a Z-average size (alternatively called the Z-average mean or the harmonic intensity averaged particle diameter, optionally as defined in ISO 13321 or ISO 22412 standards), as determined for example by dynamic light scattering, of 1000 nm or less, 700 nm or less, or 500 nm or less. In some contexts or countries, or according to some definitions, such particles may be called microparticles rather than nanoparticles, particularly if they have a size greater than 100 nm, which is optional. In other alternatives, the nanoparticles may have a Z-average size of 20 nm or more.

The word "fluorescein" is used colloquially and refers to fluorescein related compounds which include fluorescein; fluorescein derivatives (for example fluorescein amine, fluorescein isothiocyanate, 5-carboxy fluorescein, carboxyfluorescein succinimidyl esters, fluorescein dichlorotriazine (DTAF), 6-carboxy-4',5'-dischloro-2',7'-dimethoxyfluorescein (JOE)); and, isomers of fluorescein and fluorescein derivatives. Although the examples described herein are based on fluorescein, other fluorophores may be used, for example rhodamine or others, with adjustments to the light source and/or sensor if required. For example, rhodamine B can be excited by a green LED and photographed with a sensor having an emission bandpass filter with a CWL in the range of 560-580 nm.

The examples describe handheld intra-oral devices. However, in other alternatives various components of the device, for example lamps, filters and sensors, can be placed in or near a mouth as parts of other types of intra-oral devices or oral imaging systems. Multiple sensors may also be used. For example, the device may be a partial or whole mouth imaging device or scanner operated from either a stationary or moving position in or near the mouth. Although the intra-oral device described in the examples is intended to produce an image of only one or a few teeth at a time, in other alternatives a device may produce an image of many teeth, either as a single image or as a composite produced after moving the device past multiple teeth.

The article—*Carious Lesions: Nanoparticle-Based Targeting and Detection of Microcavities*—Advanced Healthcare Materials Vol. 6 No. 1 Jan. 11, 2017 (Adv. Healthcare Mater. January 2017) is incorporated herein by reference. This article describes cationic starch-based fluorescent nanoparticles. The nanoparticles are attracted to carious lesions and glow under a dental curing light. International Publication Number WO 2017/070578 A1, Detection and Treatment of Caries and Microcavities with Nanoparticles, published on Apr. 27, 2017 is also incorporated by reference.

In further examples, any of the systems described above are modified to have blue lights having a peak wavelength that is less than 480 nm, for example in the range of 400-465 nm or 425-465 nm or 435-450 nm without using an excitation filter over the blue lights. The lights may be blue LEDs. Light in this wavelength does not excite fluorescein to the same extent as light of a higher frequency. However, the inventors have observed that the ability to detect the nanoparticles against the background of fluorescent enamel, optionally using software, may be improved with the lower frequency of light. Without intending to be limited by theory, the improvement might result from reduced activation of green pixels in a standard RGD camera sensor by reflected blue light relative to blue light of of a higher wavelength, from a reduction in the amount of light being above about 500 nm considering that LEDs produce some light above and below their peak wavelength, or from an increase in hue separation between intact enamel and an exogenous fluorescent agent. Further, a very low wavelength blue light, for example in the range of 400-434 nm, or 400-424 nm, might not offer an improvement in terms of detecting an area with fluorescent nanoparticles, but may allow for a barrier filter with a lower cut on frequency to be used. An image created through a barrier filter with a cut on frequency near the top of the blue range, i.e. 450 nm or more or 460 nm or more, may provide an image that looks more like a white light image, or that is more able to be color balanced to produce an image that looks more like a white light image. Optionally, adding some red light (which may be provided by a red LED, purple LED or low-medium color temperature white LED) may further improve the ability to color balance the resulting image to produce an image that looks more like a white light image. Merging a blue light image with an image taken under white light, whether the white light image is take through the barrier filter or not, may also improve the ability to color balance the resulting image to produce an image that looks more like a white light image In one example, spectrometer readings indicated that a blue LED with a nominal peak wavelength in the range of 469-480 nm still output about 5% of its peak power at 500 nm and above. In the absence of an excitation filter, this appears from various test images to create sufficient blue light reflection and/or natural fluorescence of the intact tooth enamel to reduce the contrast between intact enamel and the exogenous fluorescent nanoparticles. Optionally, an excitation filter, for example a short pass or bandpass filter with a cut-off in the range of 480-505 nm, or in the range of 490-500 nm, may be used in combination with this blue LED to reduce the amount of over 500 nm light that is emitted. Optionally, the excitation filter has a sharp cut off as provided by a dichroic (i.e. reflective coated) filter. However, a gel or transparent plastic absorption type excitation filter may also be used.

Images were analyzed in both the red, blue, green (RGB) and hue, saturation, value (HSV) systems. Table 1 shows the HSV values, and Table 2 shows the RGB values, for intact enamel and an active lesion with fluorescent nanoparticles in an image of an extracted tooth taken under three combinations of blue LED and a longpass barrier filter over the camera sensor in three intraoral cameras similar to device 200 described above. The lesion was isolated by visual inspection and drawing a border around it. Similarly, areas of intact enamel were identified by visual inspection and drawing borders around them. After removing any completely black or completely white pixels, areas of intact enamel were concatenated together into a composite image, and areas with fluorescent nanoparticles were concatenated together into a composite image. The HSV and RGB values of the composite images were then determined.

TABLE 1

| | H (mean) | S (mean) | V (mean) |
|---|---|---|---|
| Case A lesion | 103 | 0.76 | 148 |
| Case A enamel | 100 | 0.92 | 56 |
| Case A differential | 3 | 0.17 | 93 |
| Case B lesion | 76 | 0.76 | 192 |
| Case B enamel | 46 | 0.92 | 52 |
| Case B differential | 29 | 0.16 | 141 |
| Case C lesion | 126 | 0.66 | 211 |
| Case C enamel | 134 | 0.72 | 85 |
| Case C differential | −12 | 0.05 | 127 |

TABLE 2

| | R (mean) | G (mean) | B (mean) |
|---|---|---|---|
| Case A lesion | 79 | 148 | 64 |
| Case A enamel | 20 | 56 | 36 |
| Case A differential | 59 | 93 | 28 |
| Case B lesion | 157 | 192 | 63 |
| Case B enamel | 52 | 41 | 35 |
| Case B differential | 105 | 151 | 28 |
| Case C lesion | 75 | 211 | 89 |
| Case C enamel | 23 | 85 | 43 |
| Case C differential | 52 | 127 | 46 |

In case A, the LED has a peak intensity (as specified by the manufacturer) in the range of 469-480 nm. The barrier filter is a Wratten 15, which is a longpass filter with a cut on frequency (50% transmission) of roughly 530 nm, with a somewhat rounded cut-on profile. In case B, the LED has a peak intensity (as specified by the manufacturer) in the range of 440-445 nm. The barrier filter is a Wratten 15. In case C, the LED has a peak intensity of about 405 nm. The barrier filter is a longpass filter with a cut-on frequency of about 460 nm.

While the images were taken under similar conditions, it is difficult to get completely comparable images. For example, the lights in Case A are brighter than the lights in Case B and also create a strong response from the nanoparticles. This initially caused saturation of many of the green pixels, and so for Tables 1 and 2 the power supplied to the lights in Case A was reduced. For further example, the barrier filter in Case C allows more light to pass through. The camera has an auto-exposure function, but the auto-exposure function does not react to all light and filter combinations equally. Optionally, a comparison could be made between images that are further equalized, for example to have the same V or green pixel value, for example for either the enamel region, the fluorescent nanoparticle region or the image as a whole. In the absence of such adjustment, the differential values are considered to be more useful than absolute values for comparing the cases, although even the differential values are affected by, for example, the overall brightness of the light source or exposure of the image. However, in other examples described further below it was determined that absolute values can be useful in analyzing multiple images made with a selected case (i.e. light and filter combination), although differential values may also be used.

As shown in Tables 1 and 2, case B has multiple indicators, for example H differential, V differential and green pixel differential, that are material and can be used to separate areas on the image with nanoparticles (i.e. active lesion) from areas on the tooth with intact enamel. While R differential is also significant, red fluorescence can be associated with porphorins produced by bacteria and might lead to false positives if used to detect fluorescent nanoparticles. Other tests used the 440-445 nm blue light and a Wratten 12 filter, which is a longpass filter with a cut on frequency (50% transmission) of roughly 520 nm, with a somewhat rounded cut-on profile. With this combination, relative to case B, the blue pixel differential increased and became a potentially useful indicator of the presence of the nanoparticles.

Case A has lower differentials in this example, and in particular less hue separation between the active lesion and intact enamel. In other examples, Case A might provide larger V or green pixel differentials than in Tables 1 and 2, but still typically less than in Case B, and with the hue separation consistently low.

Case C is inferior to Case B but still has useful H, V and green pixel differentials. While the H differential for case C is numerically small in this example (about 12), in other examples Case C gave a larger hue differential (up to 24). Hue differentials are resilient to differences, for example in camera settings (i.e. exposure time), applied light intensity, and distance between the camera and the tooth, and very useful in separating parts of the image with and without the exogenous fluorescent agent. For example, hue differentials persist in overall dark images whereas V or green pixel differentials typically decrease in overall dark images. Accordingly, a small hue differential, for example 5 or more or 10 or more, is useful in image analysis even if it is not as numerically large as, for example, the V differentials in this example.

Case C also preserves more blue pixel activation. The lower wavelength of the blue light source allows a lower cut on frequency of the barrier filter. Relative to Case A and Case B, this increase in blue pixel activation creates the possibility of using image manipulation, for example color balancing, to create an image that appears like a white light image, an unfiltered image, or an image taken without the exogenous fluorescent agent. To increase the amount of information available for such manipulation, a red light may be added to increase the amount of red channel information available. For example, a camera may have one or more red lights illuminated simultaneously with one or more blue lights. In this example, purple LEDs are particularly useful as the red lights since more purple LEDs are required relative to monochromatic red LEDs and so purple LED light can be dispersed more evenly distributed. The image can be manipulated to produce an image that enhances the fluorescent area and/or an image that de-emphasizes the fluorescent area or otherwise more nearly resembles a white light image. In some examples, one or two red lights are illuminated simultaneously with 4-8 blue lights. Alternatively or additionally, two separate images can be taken, optionally in quick succession. A first image is taken under blue light, or a combination of blue light and red light. This image may be used to show the fluorescent area. A second image is taken under white and/or red light. This image may be used to represent a white light image, optionally after manipulation to counter the effect of the barrier filter. As discussed above, an intraoral camera may have multiple colors of light that can be separately and selectively illuminated in various combinations of one or more colors. The techniques described herein for Case C and also be applied to other light and filter combinations, for example Case A and Case B. However, the higher cut on frequency of the barrier filter in Case A and Case B makes manipulation to produce an image resembling a white light image more difficult. However, the manipulation can still be done. In particular, when using machine vision, machine learning and/or artificial intelligence, it does not matter much whether the image would appear like an ordinary white light image to a patient. An image with increased reflected light relative to fluorescent light can be useful in an algorithm as a substitute for a true white light image (i.e. an unfiltered image taken under generally white light, optionally without an exogenous fluorescent agent) even if to a person the image might appear unnatural, for example because it has a reddish color balance. However, particularly in Case A or Case B, a filter switcher can be used. The filter switch selectively places the barrier filter in front of the sensor while lighting the blue LEDs (optionally in combination with one or more red lights) to take a fluorescence image. Alternatively, the filter switcher can remove the barrier filter from the path of light to the sensor while lighting the white and/or red LEDs to take a white light image. An image taken without the barrier filter, even if the exogenous fluorophore is present, emphasizes reflected light information over fluorescent light information and can be considered a white light image and/or used in the manner of a white light image as described herein. Such an image is also easier for a practitioner or patient to understand without manipulation, or to manipulate to more nearly resemble a white light image taken without a barrier filter and without the exogenous fluorescent agent. Optionally, the relative amount of fluorescence can be further reduced by using red-biased white light. Red-biased white light can be produced by a mixture of monochromatic red LEDs and white lights and/or by using low-medium color temperature white lights. As mentioned above, although more manipulation may be required, an image taken with the barrier filter in place, and with the fluorescent agent present, can also be used as a white light image with image manipulation, such as color balancing, used to adjust the image to make an image that appears to have been taken without a filter, particularly in Case C.

In an alternative method, the ratio of G:B can be used to distinguish areas of the exogenous fluorescent agent from areas of intact enamel. Using a ratio, similarly to using the H value in the HSV system, may be less sensitive to variations in light intensity, camera exposure time etc. Optionally, an intraoral camera may have two or more sets of blue LEDs, optionally with different peak frequency. The presence of the fluorescent agent in one image may be confirmed in the second image. Using two images can be useful, for example, to identify areas that are unusually bright (for example because of glare or direct reflection of the reflective cavity of the LED into the sensor) without containing nanoparticles or dark (for example due to shadows) despite the presence of nanoparticles. If the second set of LEDs are located in different positions than the first set of LEDs, then the pattern of reflections and reflections will be different in the two images, allowing reflections and shadows to more easily be identified and removed. If the two sets of LEDs have different shades of blue, then more ratiometric analysis techniques are available. For example, considering Case A and Case B above, the green pixel intensity should increase in the enamel and decrease in a lesion in the Case A image relative to the Case B image. The presence of these changes can be used to confirm that an area is enamel or lesion.

In some examples, blue channel intensity and/or blue differential are used to locate a florescent area of an image. Although blue channel intensity and differential are smaller than green channel intensity and differential, the green channel is more likely to become saturated. Since early stage lesions are typically small, the lesion does not heavily influence a typical camera auto-exposure function. An auto-exposure function may therefore increase exposure to the point where the green channel is saturated in the fluorescent area, and possibly in areas bordering the fluorescent area. However, the blue channel is not saturated. Comparing blue channel intensity to a threshold value can reliably determine which pixels are in a fluorescent area of an image.

The intraoral camera may have the sensor displaced from the end of the camera that is inserted into the patient's mouth rather than in the end of the camera as in FIG. 4. For example, the sensor may be displaced from the camera by a distance of at least 20 mm, at least 30 mm or at least 40 mm, or such that the sensor is generally near the middle of the camera. An angled mirror can be placed at the end of the camera that is inserted into the patient's mouth to direct the image to the sensor. This arrangement provides a longer light path and thereby provides more room for, for example, a filter switcher and/or a tunable (i.e. focusing) lens. A tunable lens may be, for example, an electro-mechanically moving lens or a liquid lens. Optionally, one or more additional fixed lenses may be placed between the sensor and the mirror. The increased distance between the tooth and the sensor can also increase the focal range of the camera.

In one example, a filter switcher has a barrier filter mounted to the camera through a pivot or living hinge. An actuator, for example a solenoid or muscle wire, operates to move the barrier filter between a first position and a second position. In the first position, the barrier filter intercepts light moving from outside of the camera (i.e. from a tooth) to the sensor. In the second position, the barrier filter does not intercept light moving from outside of the camera (i.e. from a tooth) to the sensor. In this way, the camera can selectively acquire a filtered image or an unfiltered image. In one example, the camera is configured to collect images in one of two modes. In a first mode, a white or red light is illuminated while the barrier filter is in the second position to produce an unfiltered image. In a second mode, a blue light is illuminated, optionally in combination with a red light, while the barrier filter is in the first position to produce a filtered image. Using one or more buttons on the body of the camera or a command initiated from a controller (i.e. a computer or a remote operating device such as a foot pedal), an operator may instruct the camera to produce a filtered image, an unfiltered image, or a set of images including a filtered image and an unfiltered image. Optionally, the filtered image and the unfiltered image are taken in quick succession to minimize movement of the camera between the images. This helps to facilitate comparison of the two images, or registration of one image with another for combination of the images or parts of the images.

In an example, a camera is made with a sensor coupled with a tunable lens placed inside the camera. A fixed lens is placed in front of, and spaced apart from, the tunable lens.

A mirror angled at 45 degrees is placed at the end of the camera. Optionally, a filter switch is placed between the fixed lens and the mirror. A clear cover glass is placed over the mirror to enclose the camera. In one example, rows of three to five LEDs are placed on the outside of the camera on one or more sides of the cover glass. Optionally, the LEDs may be covered with a diffuser and/or an excitation filter. Optionally, the LEDs may be angled as described above in relation to FIG. 4. In another version, LEDs are located inside the camera and arranged around the sensor. Optionally, a camera may have a liquid lens, a solid lens and an imaging element as described in U.S. Pat. No. 8,571,397, which is incorporated herein by reference. A mirror and/or a filter switcher may be added to this camera, for example between the liquid lens and the solid lens, between the solid lens and the imaging element, or beyond the liquid lens (i.e. on the other side of the liquid lens from the imaging element).

Optionally, an edge detection algorithm may be used to separate one or more teeth in an image from surrounding tissue. Very large carious lesions are apparent to the eye and typically active. The fluorescent nanoparticles are most useful for assisting with finding, seeing and measuring small lesions or white spots, and for determining if they are active. In this case, most of the tooth is intact and one or more measurements, for example of H or V n the HSV system, or G or B in the RGB system, taken over the entire tooth is typically close to the value for the enamel only. These values can then be used as a baseline to help detect the carious lesion. For example, the carious lesion (i.e. florescent area) may be detected by a difference in H, V, G or B from the baseline. Alternatively, an edge detection algorithm may also be used to separate an active carious lesion (with fluorescent nanoparticles) from surrounding intact enamel. Once separated, the active carious lesion can be marked (i.e. outlined or changed to a contrasting color) to help visualization, especially by a patient. The area of the active carious lesion can also be measured. Optionally, the active carious lesion portion may be extracted from a fluorescent image and overlayed onto a white light image of the same tooth.

References to "hue" in this application can refer to the H value in an HSV, HSL or HSI image analysis system. In some examples, a ratio of the intensity of two or three channels in an RGB system is used in the same manner as hue.

It is expected that the methods and devices described above could also be used to image fluorescein targeted to other parts of the mouth. For example, aqueous sodium fluorescein may be used to help image plaque.

In some examples, image analysis includes isolating one or more teeth in an image from surrounding tissue, for example using an edge detection or segmentation algorithm. Optionally, the area outside of the tooth may be removed from the image. Optionally, various known algorithms, such as contrast enhancement algorithms or heat map algorithms, may be used to improve visualization of features of the tooth. Improved visualization may help with further analysis or in communication with a patient.

Images may be analyzed in the RGB system, wherein each pixel is represented by 3 values for red, green and blue channel intensities. Alternatively, images may be analyzed in another system, for example a system having a pixel value for hue. In the HSV system, for example, hue (or color) is represented in a scale of 0-360 wherein green hues have values in the range of about 70-160.

For a selected blue light and filter combination, the hue of light produced by fluorescent nanoparticles is generally consistent between images. In one example, selecting pixels with a hue in the range of 56.5 to 180 reliably identified pixels corresponding to the parts of images representing the fluorescent nanoparticles. However, appropriate hue range may vary depending on the wavelength of blue light and filter used, and so a different hue range may be appropriate for a different camera. Once pixels representing the fluorescent nanoparticles, which cumulatively represent a fluorescent area, are identified, the image may be optionally modified in various ways to emphasize, or help to visualize, the fluorescent area. For example, pixels representing the tooth outside of the fluorescent area may be reduced in intensity or removed. In other examples, a contrast enhancement algorithm may be applied to the image, optionally after reducing the intensity of or removing the image outside of the fluorescent area. In other examples, a Falzenszwalb clustering or K-means clustering algorithm is applied to the image, optionally after reducing the intensity of or removing the image outside of the fluorescent area. In other examples, a heat map algorithm is applied to the image, optionally after reducing the intensity of or removing the image outside of the fluorescent area. In other examples, the fluorescent area is converted to a different color and/or increased in intensity, optionally after reducing the intensity of or removing the image outside of the fluorescent area.

The standard clinical guidelines for diagnosis of carious lesions are detection of the lesion, determination of lesion activity and a scoring of severity to determine treatment. Earlier stage lesions can be treated medically with fluoride and cleanings, whereas more advanced cavitated lesions may require surgical treatment and operative repair. Detection and treatment of earlier stage lesions can reduce long-terms costs, the need for operative management, and decrease rates of complication from advanced disease.

To aid dentists in the detection and scoring of lesion severity and activity, multiple clinical scoring systems for carious lesions have been designed and validated including the NYVAD criteria and ICDAS system. Yet, both clinical detection systems suffer from poor accuracy on activity and severity scoring, especially with earlier stage lesions, in addition to requiring significant training and time commitment from dentists to use in a clinical setting. For both systems, trained dentists have the lowest sensitivity, specificity, and inter-rater agreement for earlier stage (non-cavitated) lesions. Estimates for accuracy for ICDAS severity scoring can range from 65-83%, with lower accuracies for earlier stage lesions. Although few studies exist comparing these systems to gold standards for lesion activity, one study found an accuracy of 52% for dentists determining lesion activity using the ICDAS system. Moreover, general practitioners find these systems too complicated, time consuming and costly to use in practice and thus their utilization is low. In real-world practices, identification of severity, particularly early lesions, and lesion activity is likely worse than being reported in the literature with these systems.

Machine learning (ML) and artificial intelligence (AI) have been reported as a potential solution for highly accurate and rapid detection and scoring of dental caries. Most studies have been using radiographic images with accuracies exceeding 90%, yet these studies lack scoring of lesion severity or activity and are dependent on radiographs being obtained and the resolution limits of radiography. One study has been reported using an intraoral camera to obtain white-light images to detect and score occlusal lesions using the ICDAS system. This study achieved reasonable success, but the model performed poorly on lower severity lesions with reported F1 scores for ICDAS 1, 2 and 3 of 0.642, 0.377, 0.600 respectively. This study also did not include a determination of lesion activity.

Targeted fluorescent starch nanoparticles (TFSNs) have been shown to bind to carious lesions with high surface porosity, thought to be an indicator of lesion activity. Their intense fluorescence and specific targeting allow for dentists to visually detect carious lesions, including very early-stage lesions with high sensitivity and specificity. As the particle fluorescence enhances visual signal and is thought to be related to lesion activity, here we study whether ML on images of teeth labeled with TFSNs can be used for detection of carious lesions and scoring of activity and severity using the ICDAS scale. Moreover, as the fluorescent signal is intense and unique, the signal can be extracted from images for quantification and/or image augmentation for potential benefit in machine learning, disease classification and patient communication.

In an experimental example, 130 extracted human teeth with a range of caries severities were selected and imaged with a stereomicroscope under white-light illumination, and blue-light illumination with an orange filter following application of the FOSS particles. Both sets of images were labeled by a blinded ICDAS-calibrated cariologist to demarcate lesion position and severity. Convolutional Neural Networks were built to determine the presence, location, ICDAS score (severity), and lesion surface porosity (activity) of carious lesions, and tested by 20 k-fold validation for white-light, blue-light, and the combined image sets. This methodology showed high performance for the detection of caries (sensitivity 89.3%, PPV 72.3%) and potential for determining the severity via ICDAS scoring (accuracy 76%, SD 6.7%) and surface porosity (activity of the lesions) (accuracy 91%, SD 5.6%). More broadly, the combination of bio-targeted particles with imaging AI is a promising combination of novel technologies that could be applied to many other applications.

Human teeth that were anonymously donated to the University of Michigan were autoclaved and selected for the study to have a variety of carious lesion severities on the occlusal surface. Teeth with severe staining, calculus, and/or restorations were excluded. Teeth were immersed in a 1.0% w/w dispersion of TFSNs in deionized water (substantially similar to TFSNs later made commercially available as LumiCare™ from GreenMark Biomedical) for 30 seconds, then were rinsed for 10 seconds in deionized water to wash away unbound TFSNs. These teeth were then imaged at 10× magnification using a Nikon Digital Sight DS-Fi2 camera mounted on a Nikon SMZ-745T stereomicroscope. White light images were taken with white light illumination and autoexposure; blue light images were taken with illumination by an Optilux 501 dental curing lamp and using a light orange optical shield longpass filter, of the type frequently used by dental practitioners to protect their eyes from UV or blue light exposure. The blue light images include fluorescence produced by the TFSNs.

Figure 5:
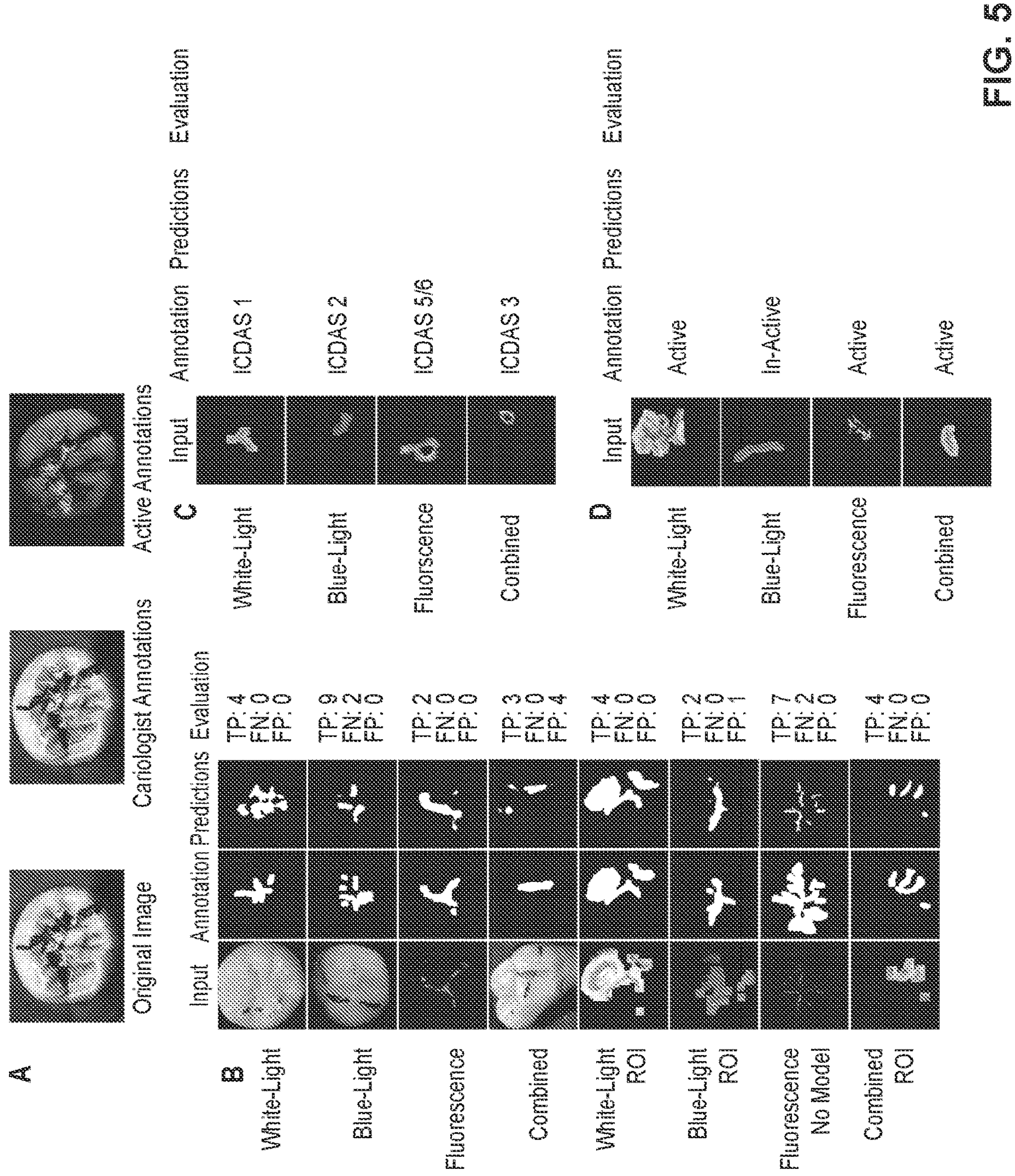
FIG. 5 is a pictorial representation of an image analysis process.
Figure 6:
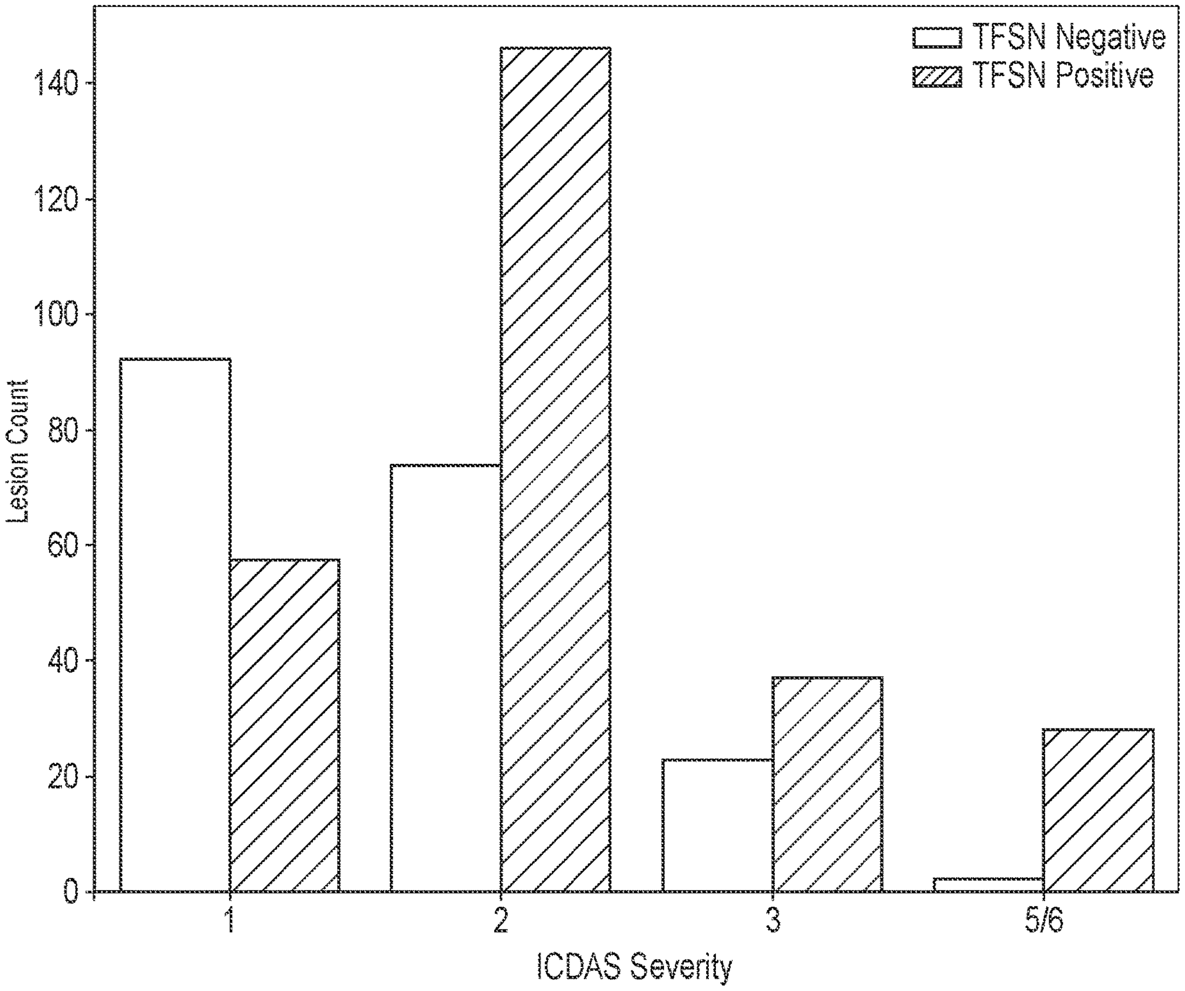
FIG. 6 is a graph of active and inactive lesions of varying severity for a set of extracted teeth.

Images were annotated by an ICDAS-calibrated human examiner (cariologist) using PhotoPea image software (www.photopea.com). The examiner used the white-light image to select and annotate lesion areas and labeled them with their corresponding ICDAS score (FIG. 5, panel A). These annotations were transferred to the blue-light images where the presence of TFSN fluorescence in the annotated lesion, as a marker for lesion activity, was determined by the examiner.

In all images, extraneous background pixels were removed by cropping to the edge of teeth using standard Sobel Edge Detection methods. All images were resized to 299×299 pixels for input into neural networks.

On a subset of 40 blue-light images, fluorescent and non-fluorescent regions were manually annotated. Pixel values were extracted as three-dimensional hue-saturation-intensity (HSI) with their corresponding fluorescent or non-fluorescent label. A decision tree classifier was trained to determine whether a pixel was fluorescence or not, and a 20 k-fold cross-validation found accuracy of this method at 99.98% within the labeled dataset. A model trained on the entire dataset of pixels from the 40 annotated images was applied to the remaining blue-light images for isolation of TFSN fluorescence.

As it was not known which input images would be best for different machine learning tasks, all variations of images were generated. First, white-light, blue-light and images with only the extracted fluorescent pixels (called "fluorescence" for brevity) were generated and processed. As we know the TFSN fluorescence targets known lesions and surface porosity, the extracted fluorescent pixels could be used to identify regions of interest (ROI) in images, areas of isolated fluorescence expanded by 10-contiguous pixels. Fluorescent pixels could also be added back to white-images as a high-contrast blue scaled to intensity (or other augmented area) to create 'combined' (or augmented) blue-light, white-light images. A blue-scale was selected for the combined images to maximize contrast, as blue hues did not overlap with any existing hues in the white-light images. As input for models to determine lesion location, white-light, blue-light, combined, isolated fluorescence (called "fluorescence" in FIG. 5), and all forms of ROI images were tested (FIG. 5, panel B). As an additional baseline for determining lesion location, isolated fluorescence was used without a model (called "fluorescence no model" in FIG. 5), where the isolated fluorescence determined by the decision tree classifier (using hue and intensity as the classification parameters) was directly converted to a prediction mask (FIG. 5, panel B). As input for models to determine lesion surface porosity and lesion severity, lesion pixels were extracted from entire image for white-light, blue-light, combined, and isolated TFSN images for all lesions (FIG. 5, panels C and D).

Determination of lesion presence and location is a semantic segmentation machine learning task. U-Net model architectures have been shown to be very effective at these tasks, including for biomedical images. Thus, we decided to use a U-Net model architecture for this task. These models require a mask as output and so lesions were converted into binary masks for model training and evaluation (FIG. 5, panel B).

Determination of lesion severity and activity from an isolated lesion is an image classification task. Convolutional Neural Networks (CNNs) have been shown to be incredibly effective at these tasks. NASnet is a CNN architecture that has achieved state-of-art results on many benchmark image classification tasks. Thus, we used the NASNet architecture for our classification models. Separate models were trained and evaluated for both scoring severity and lesion activity (FIG. 5, panels C and D).

All models were trained and evaluated using a 30 k-fold cross-validation. For each fold, the model trained for 60 epochs with Adam optimization.

A standard measurement of model performance for semantic segmentation tasks is intersection-over-union (IOU), which is defined as the ratio of pixels predicted by a model that overlap with pixels in the annotation mask divided by the sum of pixels predicted and in the annotation mask, where a value of 1 would be a perfect prediction. This metric is stringent in that small deviations can result in large numbers of non-overlapping pixels and a lower IOU that might not reflect clinical relevance. We also determined rates of true positives, false negatives, and false positives to determine sensitivity and positive-predictive value (PPV) (FIG. 5, panel A). True positives were defined as a contiguous region of pixels that overlapped with a known lesion. False negatives were when a lesion had no overlap with predicted regions. A false positive was a region of pixels predicted that had no overlap with a known lesion. Overall, IOU, sensitivity and PPV were calculated per k-fold. The average and standard deviation was determined across all 30 folds. For models that used the isolated TFSN fluorescence or regions of interest as input, they were evaluated only against lesions that were determined to be active as other lesions would have been removed from the image. As we had the lesion severities and activity, sensitivities could also be calculated for each ICDAS severity score and activity status.

For classification models, the predicted classification of the model was compared to the true label to determine overall accuracy scores and F1 scores, the harmonic mean of specificity and sensitivity. These metrics were determined per k-fold and the mean and standard deviation across all 30 folds was calculated. These metrics were calculated per sub-class in the classification task (activity or ICDAS severity).

On the 130 images of teeth, 459 lesions were identified and annotated by the ICDAS-calibrated examiner. No ICDAS 4 lesions were identified. Most lesions were ICDAS 1 or 2 in severity with very few ICDAS 3's or 5/6's. On manual review, 268 of the 459 lesions had TFSN fluorescence suggesting that 58.4% of lesions were active/had surface porosity.

Overall utilizing the complete combined images performed the best with a mean sensitivity of 80.26% and PPV of 76.26% (Table 3). Across all models, sensitivity increased with increasing ICDAS severity. Models being fed the 'regions of interest' performed nearly as well as models with the entire tooth.

TABLE 3

| Input | Sub-class | IOU Mean | Sensitivity (%) | PPV (%) |
|---|---|---|---|---|
| White-Light | Overall | 32.38 (8.0) | 79.15 (12.79) | 75.72 (11.33) |
| | Active | — | 81.42 (15.6) | — |
| | Inactive | — | 75.45 (18.85) | — |
| | ICDAS 1 | — | 70.21 (30.43) | — |
| | ICDAS 2 | — | 81.38 (15.65) | — |
| | ICDAS 3 | — | 88.1 (20.2) | — |
| | ICDAS 5/6 | — | 94.44 (22.91) | — |
| Blue-Light | Overall | 28.92 (7.64) | 72.39 (13.94) | 74.31 (14.24) |
| | Active | — | 75.4 (15.87) | — |
| | Inactive | — | 67.57 (24.06) | — |
| | ICDAS 1 | — | 61.64 (31.21) | — |
| | ICDAS 2 | — | 75.27 (17.71) | — |
| | ICDAS 3 | — | 78.81 (31.88) | — |
| | ICDAS 5/6 | — | 91.67 (25.0) | — |
| Fluorescence | Overall | 16.0 (10.23) | 59.92 (25.9) | 63.04 (28.21) |
| | ICDAS 1 | — | 32.69 (39.35) | — |
| | ICDAS 2 | — | 60.09 (33.79) | — |
| | ICDAS 3 | — | 73.86 (36.09) | — |
| | ICDAS 5/6 | — | 86.27 (32.46) | — |
| Combined | Overall | 31.17 (7.96) | 80.26 (12.33) | 76.36 (12.86) |
| | Active | — | 80.11 (15.15) | — |
| | Inactive | — | 79.28 (21.62) | — |
| | ICDAS 1 | — | 68.07 (28.9) | — |
| | ICDAS 2 | — | 84.89 (13.17) | — |
| | ICDAS 3 | — | 83.94 (25.43) | — |
| | ICDAS 5/6 | — | 91.67 (25.0) | — |
| White-Light ROI | Overall | 32.38 (11.66) | 77.2 (19.27) | 76.01 (19.63) |
| | ICDAS 1 | — | 65.79 (37.64) | — |
| | ICDAS 2 | — | 72.95 (31.5) | — |
| | ICDAS 3 | — | 83.33 (34.45) | — |
| | ICDAS 5/6 | — | 94.12 (23.53) | — |
| Blue-Light ROI | Overall | 27.04 (11.66) | 72.11 (19.85) | 72.97 (22.9) |
| | ICDAS 1 | — | 45.98 (38.74) | — |
| | ICDAS 2 | — | 73.81 (28.23) | — |
| | ICDAS 3 | — | 78.79 (35.24) | — |
| | ICDAS 5/6 | — | 94.12 (23.53) | — |
| Combined ROI | Overall | 33.4 (11.29) | 78.69 (16.75) | 69.45 (19.5) |
| | ICDAS 1 | — | 62.48 (36.9) | — |
| | ICDAS 2 | — | 79.31 (29.04) | — |
| | ICDAS 3 | — | 83.33 (30.98) | — |
| | ICDAS 5/6 | — | 94.12 (23.53) | — |
| Fluorescence without Model | Overall | 11.13 (5.97) | 57.42 (23.9) | 47.31 (22.92) |
| | ICDAS 1 | — | 24.91 (32.73) | — |
| | ICDAS 2 | — | 61.11 (31.94) | — |
| | ICDAS 3 | — | 65.91 (38.43) | — |
| | ICDAS 5/6 | — | 86.27 (32.46) | — |

Figure 7:
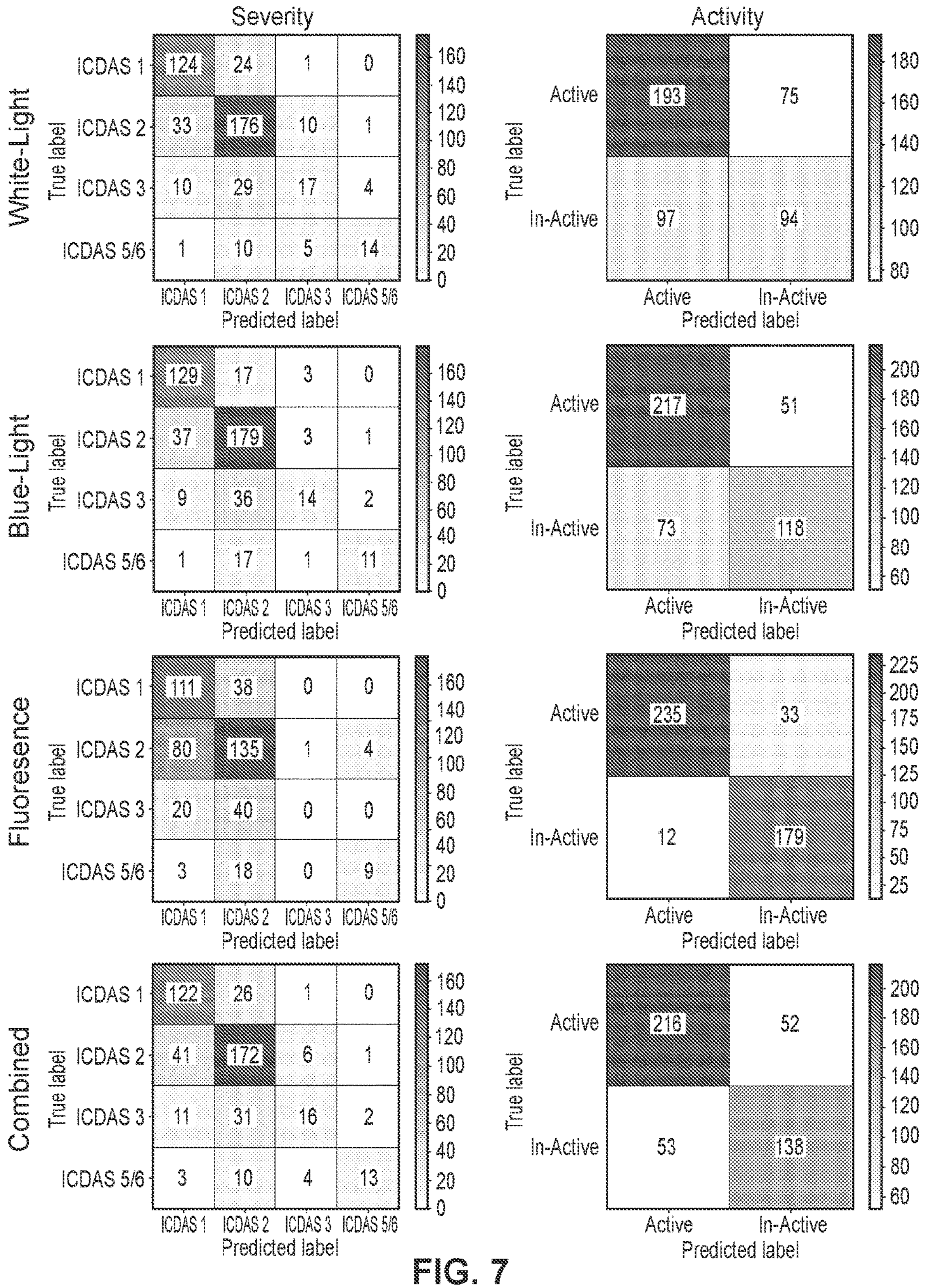
FIG. 7 are results of lesions scored using software applied to different types of images compared to lesions scored by a person.

Overall, the models using blue-light and white-light images had the highest accuracies, both at 72% (Table 4). The highest F1 scores were generally for lesions with lower ICDAS severity scores, ICDAS 1's and 2's (Table 4). Confusion matrices for all inputs and models for severity scoring are shown in FIG. 7.

Using isolated fluorescence alone had an overall accuracy of 90% for determining lesion activity (Table 4). Using white-light images, the model's accuracy at predicting lesion activity was 63%, minimally better than would be expected of chance (58.4%), assuming the model always predicted a lesion was active (Table 4). Confusion matrixes for all inputs and models for activity scoring are shown in FIG. 7.

TABLE 4

| Input | ICDAS Class | Mean F1 | Activity | Mean F1 |
|---|---|---|---|---|
| White-Light | 1 | 0.78 (0.09) | Active | 0.69 (0.08) |
| | 2 | 0.77 (0.07) | | |
| | 3 | 0.37 (0.34) | In-Active | 0.52 (0.15) |
| | 5/6 | 0.57 (0.49) | | |
| | Total Accuracy | 72% (5.67%) | Total Accuracy | 63% (10.0%) |
| Blue-Light | 1 | 0.79 (0.11) | Active | 0.78 (0.10) |
| | 2 | 0.76 (0.09) | | |
| | 3 | 0.34 (0.31) | In-Active | 0.66 (0.15) |
| | 5/6 | 0.50 (0.47) | | |
| | Total Accuracy | 72% (7.55%) | Total Accuracy | 73% (11.5%) |
| Fluorescence | 1 | 0.61 (0.11) | Active | 0.91 (0.06) |
| | 2 | 0.60 (0.13) | | |
| | 3 | 0.00 (0.00) | In-Active | 0.89 (0.08) |
| | 5/6 | 0.42 (0.44) | | |
| | Total Accuracy | 56% (8.54%) | Total Accuracy | 90% (7.00%) |
| Combined | 1 | 0.75 (0.11) | Active | 0.80 (0.08) |
| | 2 | 0.75 (0.10) | | |
| | 3 | 0.37 (0.31) | In-Active | 0.72 (0.14) |
| | 5/6 | 0.57 (0.48) | | |
| | Total Accuracy | 70% (8.31%) | Total Accuracy | 77% (10.4%) |

Overall, we have shown that machine learning in combination with targeted fluorescent starch nanoparticles is a feasible method for determining the presence, location, severity, and surface-porosity of carious lesions in images of extracted teeth. This is the first attempt at using machine learning to determine carious lesion activity and is the first use of these novel technologies together.

Regarding lesion location and presence, our best models were reasonably sensitive, 80.26%, with good PPV, 76.36%. The models were most sensitive to more severe, cavitated (higher ICDAS) lesions, similar to performance by dentists, yet still had reasonable sensitivities for non-cavitated ICDAS 1 and 2 lesions.

Our models performed well on scoring ICDAS 1 and 2 lesions by their severity (F1>0.75) yet did poorly on more severe lesions. This discrepancy, particularly as compared to our high sensitivity for high ICDAS lesions and what has been reported in the literature is likely secondary to our dataset's skew, where there were not sufficient more severe ICDAS lesions for model learning.

As expected, models using images of isolated fluorescence were highly accurate at determining lesion activity, with 90% accuracy. White-light images alone as input did not result in apparent model learning, being minimally better than what would be expected by chance (63% vs 58.4%). It is possible that information regarding surface porosity is not present in these images without the added fluorescence from the TFSNs and thus determining lesion activity is an impossible task using white-light images alone. This could be supported by the data from the literature that dentist's accuracy at determining lesion activity visually could be near 50%, a chance guess. The NYVAD system, which appears to be more reliable, incorporates observations on the surface roughness (tested with a dental explorer) and response to drying, which may provide the dentist additional information on surface porosity that is not determinable by visual examination.

Pixels in a fluorescent area in a blue-light image can be located and extracted. Extraction of these pixels can be used for detection of regions of interest and lesion activity without training ML models, for example using a decision tree classification, comparison to a single parameter range or threshold, or edge detection classification, any of which may be based for example on one or more of hue and intensity. A primary concern with ML is overfitting and lack of transferability. Fluorescent extraction can act as a starting point for lesion detection and activity scoring that would be transferable across image types without the need for significant image annotation and training of models that may be susceptible to overfitting and not clinically practical. Extraction of fluorescent pixels from a blue light image, with or without an ML model, as in create a prediction mask, may also be used to augment a white light image of the same tooth, for example by overlaying the mask on the white light image, optionally after image manipulation to scale, rotate, translate or otherwise overlay two images taken in a patient that may not be initially identical in size, position or orientation of the tooth. The augmented white light image may be useful to enhance communication with a patient, for example by providing a visual indication of the size and location of an active lesion. Optionally, an augmented blue light image may also be created for patient communication by converting extracted fluorescent pixels or a mask to a selected hue or intensity. The augmented white or blue light image can offer increased contrast of the fluorescent pictures, or a more sharply defined edge, either of which can assist a patient in understanding the active area or recording the active area for further use, such as a size measurement or comparison against another image taken at a different date.

The images were labeled by an ICDAS calibrated cariologist. Unlike other studies in the literature, the use of TFSN images allowed for determination of activity in addition to lesion severity. All lesions being labeled for severity and activity allowed comparison of model performance across lesion sub-classes. Splitting up machine learning tasks allowed for comparison of performance across components of the clinical pathway.

Limitations were the small data-set size of 130 teeth with no ICDAS 4 lesions and few ICDAS 5 and 6 lesions. Moreover, these images were obtained with extracted teeth using a microscope rather than in vivo intraoral images. As noted, using an ICDAS-calibrated cariologist's visual examination from the images as the "gold standard" may limit the model's accuracy. A full clinical exam with tactile testing and drying the tooth could provide more accurate scoring. Despite these limitations, the result of this study indicates that these methods can be usefully applied to images of a patient taken with a standard (white light) intraoral camera and/or an intraoral camera with blue lights and filters as described herein.

Machine learning in combination with targeted fluorescent starch nanoparticles is a feasible method for determining the presence, location, severity, and surface-porosity of carious lesions in images of extracted teeth. Continued development of these technologies may aid dentists in fast and accurate detection and scoring of carious lesions, particularly early lesions, and promote preventive dentistry and global health and well-being.

Methods described herein can also be performed in vivo using intraoral camera images or camera images taken from outside of the mouth, for example using a digital single lens reflex (DSLR) camera or smartphone camera, optionally using mirrors and/or retractors. For images taken outside of the mouth, fluorescent images can be taken by shining a blue light, for example a curing lamp, at a tooth or multiple teeth of interest and adding a filter over the camera lens. Alternatively, a camera flash unit may be covered with a blue filter, for example a Wratten 47 or 47A filter, or an LED based flash system may be converted by removing white LEDs and replacing them with blue LEDs, to provide blue light. Suitable filters for either smartphone or DSLR cameras are available from Forward Science, normally used with their OralID™ oral cancer screening device, from Trimira as normally used for their Identifi™ oral cancer screening device or from DentLight, as normally used for their Fusion™ oral cancer screening device. Alternatively, a Tiffen 12 or 16 filter may be attached to the lends of a DSLR camera. For intraoral camera images, white light images can be taken from a conventional intraoral camera and fluorescent images can be taken from an intraoral camera with blue lights and filters as described herein. Optionally, an intraoral camera can be used to take both blue and white images. For example, a CS1600™ camera from Carestream produces a white light and a fluorescent image. However, this product seeks to identify carious lesions by way of reduced intensity relative to healthy enamel and so the software used with the camera is not suitable. Intraoral cameras that can take white light and fluorescent images are also described in US Patent Application Publication 20080063998 and 20190365236, which are incorporated herein by reference.

To determine how TFSN affects ML model transferability and overfitting, models trained using white-light and blue-light images can be tested on images with varying lighting and conditions. Additionally, the ability of our models to predict lesion severity from fluorescence alone suggests that TFSN fluorescence is variable with lesion severity and thus could be a marker of lesion severity. Metrics of fluorescence size and intensity could be studied on lesions over time to determine their predictive value of lesion progression. Fluorescent properties could also be studied in relation to lesion depth.

In an example of an in vivo process, a patient's teeth may be cleaned, followed by the patient swishing an aqueous dispersion of fluorescent nanoparticles (such as LumiCare™ from GreenMark Biomedical) in their mouth, followed by a rinse. Images or one or more teeth are obtained, for example with intra-oral camera. Optionally, both fluorescent (blue-light and barrier filter) and white-light (optionally through a low cut-on long pass filter) are obtained at the same time or close to the same time. Optionally, a fluorescent image (or a fluorescent area extracted from a fluorescent image) and a white light image are overlaid. The images are passed to software on a computer or uploaded to cloud for processing.

Individual teeth may be identified by name/location for the patient (e.g., Upper Left First Molar) either by AI or by a dentist (or other clinician). Optionally, a dentist may first first take images of all teeth as a baseline and to label images. Once enough images have been captured and labeled by the dentist, a model to identify tooth identity can be deployed for automatic labeling. Using image overlay or image similarity computations, software can identify teeth on subsequent visits and overlay images for comparison. ORB is one optional computational method of overlaying images.

A tooth is selected and one or more areas of interest are identified on the tooth. Optionally, a classifier may be used to identify and/or extract pixels representing the fluorescent nanoparticles. The identification/extraction may be based on HSI with a classifier, or a neural network for segmentation applied to find fluorescence. A decision tree (i.e. is hue within a selected range, is value or intensity above a selected threshold) has been used, but other algorithms (random forest, SVM, etc.) may also be used. The fluorescent regions can be automatically labeled, and the dentist asked to confirm the presence of lesions and score their severity.

Optionally, segmentation models can be applied on both white-light and blue-light (fluorescent) models to determine areas of interest. The use of a white light image (in addition to a fluorescent image) may improve accuracy and allows non-fluorescent (i.e. inactive) lesions to be detected. Segmentation models could be multi-class, automatically identifying ICDAS (or other) severity scores of regions of interest. Areas of interest can be scored by neural networks based on severity and other characteristics (depth, activity, etc.). Optionally, white-light and blue-light images can be used with a convolutional neural network for image classification.

The software may generate statistics regarding fluorescence amount, area of fluorescence and change in region over time as compared to prior images. Optional additional models could be for likeliness of treatment success, etc.

For neural networks used in the process described above, U NET-based architectures have worked best for segmentation tasks and variants of Convolutional Neural Networks (CNNs) have worked best for classification. As the field develops new architectures might be discovered that are superior and may be adapted to the methods described herein.

In another example, the area of fluorescent nanoparticles on a tooth was determined by selecting pixels having a hue value within a specified range. The range varies with the light and filter combination used to take the image. However, for a specified blue light source and filter, the hue range was accurate over most (i.e at least 95%) of tooth images.

In another example, four known machine learning algorithms (logistic regression (LR), linear discriminant analysis (LDA), classification and regression tree (CART) and Naive Bayes Classifier (NB)) were trained to detect fluorescent pixels on labeled pixels (over 3 million pixels) of 10 tooth images (taken under blue light and through a barrier filter of teeth treated with fluorescent nanoparticles), using the HSV/HSI values for the pixels. The algorithms were tasked with identifying pixels associated with the fluorescent nanoparticles in new images. Mean accuracies for the four algorithms were, LR: 99.7982%; LDA: 99.3441%; CART: 99.9341%; NB: 95.2392%.

In another example, an intraoral camera, similar to device 200 as described herein, was used to take images of teeth that had been treated with fluorescent nanoparticles (LumiCare™ from GreenMark Biomedical). Fluorescent and non-fluorescent areas, comprising roughly one million pixels, were human labeled on three blue light images taken from the camera. A publicly available machine learning algorithm as described in the example above was trained to predict if a pixel is in a fluorescent are (positive pixel) or not (negative pixel) using the HSI values for the pixels. The trained model was then used to identify fluorescent areas (positive pixels)

in an additional six images from the camera. The fluorescent areas had high correspondence with fluorescent areas identified by a person except for in about one half of one image that was generally darker than the other images.

In another example, 100 teeth with 339 lesions were scored for ICDAS severity by a clinician and also checked for activity using fluorescent nanoparticles. All lesions scores ICDAS 4 or more were active. More than 90% of lesions scored ICDAS 2 or 3 were active. However, only about 60% of lesions scored ICDAS 1 were active.

The number of positive pixels (i.e. pixels identified by a machine learning algorithm to contain fluorescent nanoparticles) was demonstrated to be weakly correlated with ICDAS scoring. Maximum pixel intensity within a fluorescent area was shown to have more correlation with the presence of a lesion than mean pixel intensity. Using the number of high intensity pixels within a region (defined as pixels with at least 70% of the maximum intensity) instead of the number of positive pixels, produced a better correlation with ICDAS scoring. Where pixel intensity is used in a method described herein, it may be the mean pixel intensity or maximum pixel intensity. Since pixel intensity can vary, for example with camera settings and lighting, pixel intensities are optionally analyzed relative to an internal reference (i.e. average intensity of the tooth outside of the segment of an image containing the nanoparticles), either by a ratiometric analysis (i.e. ratio of intensity within the fluorescent nanoparticle segment to an intensity outside of the segment) or by scaling (i.e. multiplying intensities in an image by a ratio of an intensity in the image to a reference intensity) or by adjusting camera settings, i.e. exposure, in post-processing until an intensity in the image resembles a reference intensity.

The fluorescent nanoparticles can be identified on an image of a tooth by machine learning algorithms on a pixel level basis. Either white light or fluorescent images can be used, with machine learning, to do ICDAS scoring. However, the white light image is not useful for determining whether lesions, particularly ICDAS 0-2 lesions, are active or inactive. Applying the fluorescent nanoparticles and taking a fluorescent image can be used to determine detect and score active lesions. Using a white light image and a fluorescent image together allows for all lesions, active and inactive, to be located and scored, and for their activity to be determined.

In another example, Fluorescent Starch Nanoparticles (FSNPs, i.e. LumiCare™ from GreenMark Biomedical) were used to assist in the visual detection of active non-cavitated carious lesions. In this study, we evaluated the combination of FSNPs with computer vision as a tool for identifying and determining the severity of caries disease.

Extracted human teeth (n=112) were selected and marked by two ICDAS-calibrated cariologists to identify a range of caries severities (sound, non-cavitated, and cavitated) on their occlusal surface. FSNPs were applied (30 second application; 10 second water rinse) to each tooth, which were subsequently imaged by stereomicroscopy with illumination by an LED dental curing lamp and filtered by an orange optical shield. Images were evaluated with basic computer image processing techniques and information on hue, saturation, and intensity was extracted (RGB vectors converted to HSI vectors). Teeth were sectioned and histology was evaluated for Downer score by three blinded examiners. Statistical comparisons were made from image-extracted values to histology scores for each lesion.

The 112 lesions represented a range of severities (Downer 0=45, Downer 1+2=29, Downer 3+4 32 38). Fluorescent areas were determined by selecting pixels with a hue in the range of 56.5 to 180, which are deemed positive pixels. Analysis of the fluorescent area showed correlations with higher lesion severity for increased area (i.e. number of positive pixels) and average pixel intensity, and highly significant correlation ($p<10e\text{-}9$, by Kruskal Wallis) for maximum pixel intensity.

These results demonstrate the potential for combining FSNPs with computer vision techniques to extract and analyze nanoparticle fluorescence patterns to help determine lesion severity (depth). The combination of targeted nanoparticles with computer vision may provide a powerful clinical tool for dentists.

In another example, Fluorescent Starch Nanoparticles (FSNPs, LumiCare™ from GreenMark Biomedical) have been shown to assist in the detection of active non-cavitated carious lesions (NCCLs). In this study, we evaluated the potential of FSNPs as a tool for monitoring the effect of fluoride treatment on smooth surface NCCLs.

Extracted human teeth (n=40) with ICDAS 2 caries lesions (white spot lesions) on smooth surfaces were selected. FSNPs were applied (30 second immersion; 10 second water rinse) to each tooth, which were subsequently imaged by stereomicroscopy with illumination by an LED dental curing lamp filtered by an orange optical shield. Teeth then underwent a 20-day treatment cycle with immersion in artificial saliva and treatment with 1,000 ppm fluoride or negative control (deionized water), either with or without acid cycling. Teeth were then again exposed to FSNPs and reimaged. Images were compared quantitatively using image analysis and qualitatively by a blinded evaluator, with a 5-point categorical scale, for each carious lesion.

After 20 days of cycling, a high percentage of samples treated with fluoride were qualitatively judged to have improved (82.4% with acid cycling and 75.0% without acid cycling) compared to negative controls (41.7% and 54.5% with and without acid cycling, respectively). By image analysis, the average change in fluorescence was determined to be −64.1±7.1% and −58.7±5.3% for fluoride, compared to +0.17±5.9% and −38.3±5.2% for the negative control, with and without cycling, respectively.

These results demonstrate the potential for FSNPs to assist in the monitoring of treatment outcomes for early active caries lesions, with a reduction in their fluorescence following a fluoride (remineralization) treatment. These particles can be used to track the efficacy of noninvasive treatments before cavitation.

Optionally, multiple surfaces of a tooth, or a set of teeth optionally including all teeth in the patient's mouth, may be evaluated, for example to provide an ICDAS or other scoring of the multiple surfaces or teeth. A composite photograph of the multiple surfaces or set of teeth may be made by assembling multiple images. Alternatively, multiple images may be analyzed separately to identify surfaces of each tooth in the set without creating an assembled image. Summative scores, for example by adding the ICDAS score of multiple lesions, may be given for multiple lesions on a tooth surface, on a whole tooth, or on a set of teeth.

Hue values, which may include hue differentials, in the HSV or HSI system are resilient to differences, for example in camera settings (i.e. exposure time), applied light intensity, and distance between the camera and the tooth, and very useful in separating parts of the image with and without the exogenous fluorescent agent. Additionally considering intensity values, which may include intensity differentials, further assists in separating parts of the image with and without the exogenous fluorescent agent. However, similar techniques may be used wherein channel intensity values in the Red, Green, Blue (RGB) system are used instead of, or in addition to, hue values. For example, with a fluorescein-based agent, the activation level (i.e. 0-255) of the green channel and/or blue channel (both of which are typically higher for pixels in a fluorescent area) is a useful measure. Green and/or blue channel intensity is preferably used as a differential measure (i.e. to locate an area of higher blue and/or green channel intensity relative to a surrounding or adjacent level of lower green channel intensity) to make the method less sensitive to camera exposure. In an alternative or additional method, the ratio of G:B channel intensity is typically higher in a fluorescent area than in sound enamel and can be used to help distinguish areas of the exogenous fluorescent agent from areas of intact enamel. Using such a ratio, similarly to using the H value in the HSV/HSI system, may be less sensitive to variations in camera exposure or other factors. Optionally, methods as described above are implemented using one or more ratios of the intensity of two or three channels in an RGB system as a proxy for hue in the HSV/HSI/HSL system. Optionally, methods as described above are implemented using green or blue channel intensity as a proxy for I or V in the HSV/HSI/HSL system.

Optionally, when using differentials rather than absolute values a segmentation, localization or edge detection algorithm may be used to, at least temporarily, to draw a border around one or more areas with noticeably different characteristics on a tooth. Optionally, the tooth may have been isolated from the whole image by an earlier application of a segmentation, localization or edge detection algorithm before drawing a border around an area within the tooth. A differential may then be determined between pixels within the border and pixels outside of the border to determine which areas are fluorescent areas. Optionally, the border may be redrawn using values from one or more non-fluorescent areas as a baseline and designating pixels as fluorescent or not based on their difference from the baseline. The fluorescent nanoparticles are most useful for assisting with finding, seeing and measuring small lesions or white spots, and for determining if they are active. In this case, most of the tooth is intact and one or more measurements, for example of H, V/I, B, G or B:G ratio, considered (i.e. by determining an average or mean value) over the entire tooth (after determining the boundary of the tooth for example by edge detection) is typically close to the value for intact enamel. One or more of these values can then be used as a baseline to help detect the carious lesion. For example, the carious lesion may be detected by a difference in H, V/I, B, G, or B:G ratio relative to the baseline.

In some of the examples described above, a white light image is used in combination with a blue light combination In other examples, a different exogenous fluorescent agent may be excited by a different color of light and/or produce florescence with different hue or other characteristics. The light source, barrier filter, and parameters used to identify a florescent area may be adjusted accordingly. In some examples, a colored light source may not be required and a white light may be used.

In any reference to a colored light of a particular type herein, a light of another type or a combination of a light and a filter may also be used. For example, a blue, red or purple LED may be replaced by any white or multicolored light source combined with a blue, red or purple filter.

While the description above refers to software or algorithms above, some of the methods may be implemented by a person. For example, a person may view or compare images. The ability of a camera to store and/or magnify an image may help a dental practitioner analyze the image. An image may also assist a dental practitioner in communicating with a patient, since the patient will have difficulty seeing inside their own mouth. In some examples, placing two images, for example a blue light image and a white light image, simultaneously on one screen or other viewing device may help the practitioner compare the images.

Methods involving a combined image may alternatively be practiced with a set of two or more images that are considered together without actually merging the images into one image, i.e. an image with a single set of pixel vectors created from two or more sets of pixel vectors. For example, two or more images (for example a white light image and a fluorescent image) can be displayed together on a screen to be viewed simultaneously. In another example, an algorithm can consider a set of two more images in a manner similar to considering a single combined image. In a combination of images, or a method considering a set of images, one or both of the images may have been manipulated and/or one or more of the images may be some or all of an original image.

In some examples, a white light image is not used for analysis, for example identification or scoring of a lesion. A white light image may be used, for example, for patient communication or record keeping. In some examples, a white light image is an image take under white light with no filter and no fluorescent agent present. In some examples, a white light image is taken in a manner that reduces the relevant influence of fluorescent light relative to reflected light compared to a fluorescent image, but a filter and/or fluorescent agent was present.

We claim:

1. An oral imaging system comprising, a plurality of light sources including a white light source and a colored light source, wherein the white light source and the colored light source may be separately illuminated;

an image sensor;

a barrier filter over the image sensor; and, a computer configured to receive an image from the image sensor and to analyze the image using a machine vision, machine learning or artificial intelligence routine to detect pixels corresponding to florescence in the image and/or to score lesions on a tooth in the image.

2. The system of claim 1 wherein the colored light source is a blue light source and the florescence is produced by an exogenous agent comprising a fluorescein-related compound.

3. The system of claim 1 wherein the computer is configured to receive an image taken while the white light source is illuminated and to analyze the image using a machine learning or artificial intelligence routine to detect and/or score lesions in the image.

4. The system of claim 1 wherein the computer is configured to locate a fluorescent area in an image using one or more of: hue, intensity, value, blue channel intensity, green channel intensity, a ratio of green and blue channel intensities, a decision tree and/or UNET architecture neural network.

5. The system of claim 1 wherein the computer is configured to score lesions using a convolutional neural network.

6. The system of claim 1 wherein the system is configured to cross-reference lesions located in an image taken while the white light source is illuminated for activity as determined in and image taken while the colored light source is illuminated.

7. A method of analyzing a tooth comprising the steps of,
applying a fluorophore to the tooth;
shining white light at the tooth;
shining colored light at the tooth;
sensing a first image while shining white light at the tooth;
sensing a second image including fluorescence emitted from the fluorophore while shining colored light at the tooth through a barrier filter; and,
analysing the second image to detect and/or score caries on the tooth.

8. The method of claim 7 wherein analysing the second image comprises using machine vision or a machine learning or artificial intelligence algorithm.

9. The method of claim 8 wherein applying a fluorophore to the tooth comprises applying cationic particles to the tooth and isolating fluorescence from the fluorophore comprises considering hue, intensity, value, blue channel intensity, green channel intensity, or a ratio of green and blue channel intensities, alone or in combination with other values.

10. The method of claim 8 wherein analysing the second image comprises applying a UNET architecture neural network.

11. The method of claim 7 wherein analysing the second image comprises using a convolutional neural network.

12. The method of claim 7 comprising sensing a third image at a later time, analysing the third image, and comparing these results to results for the first or second image to determine the progress or regression of a disease.

13. The method of claim 7 comprising analyzing the first image using a machine learning or artificial intelligence routine to detect and/or score lesions in the image.

14. The method of claim 13 comprising cross-referencing lesions detected in the first image against lesions detected in the second image to identify inactive lesions by their appearance in the first image and not in the second image.

15. The method of claim 7 comprising isolating the tooth in the first or second image by way of an edge detection or segmentation algorithm.

16. The method of claim 7 comprising annotating the first or second image and use of the annotated image in training a machine-learning algorithm.

17. The method of claim 7 comprising, in association with an area of fluorescence detected and/or isolated fluorescence in one or more images, one or more of a) recording the location of the area, b) quantifying the area, c) quantifying the fluorescence of the area, d) storing data relating to the fluorescence, e) transmitting the image from the system to a computer, f) transposing one image over another or displaying two images simultaneously, g) quantifying the size of an area of enhanced fluorescence, h) quantifying the intensity of an area of enhanced fluorescence, for example relative to background fluorescence and i) augmenting an image.

18. A method of analyzing a tooth comprising the steps of,
applying fluorescent nanoparticles to the tooth;
shining a blue LED at the tooth;
sensing an image including light emitted from the fluorescent nanoparticles through a barrier filter; and,
isolating a fluorescent area in the image,
wherein isolating a fluorescent area comprises one or more of a) considering the hue or color ratio of pixels in the image, or a difference in hue or color ratio of some pixels in the image from the hue or color ratio of other or most pixels in the image; b) considering the intensity or value of pixels or the intensity of one or more color channels in pixels in the image, or a difference in intensity or value of pixels, or the intensity of one or more color channels in pixels, in the image from the intensity or value of pixels, or the intensity of one or more color channels in pixels, of other or most pixels in the image; and/or c) analyzing the image on a pixel basis by way of a decision tree or neural network.

19. The method of claim 18 further comprising scoring the intensity of a lesion corresponding to a segment of the image containing fluorescent nanoparticles by a) considering the number of pixels in the segment, the number of pixels in the segment having an intensity above a selected threshold, the average or mean pixel intensity in the segment and/or the highest pixel intensity in the segment; and/or, b) analyzing the segment by way of a neural network.

20. The method of claim 18 further comprising the addition of scores of multiple lesions on a tooth or multiple teeth in a mouth to determine summative scores on a per tooth surface, per tooth, or total mouth basis.

21. An oral imaging system comprising,
a first blue light source;
one or more of a red light source, a white light source and a second blue light source, wherein the light sources comprise two sets of light sources that may be separately illuminated;
an image sensor; and,
a barrier filter.

* * * * *